US010600499B2

(12) United States Patent
Jain

(10) Patent No.: US 10,600,499 B2
(45) Date of Patent: Mar. 24, 2020

(54) SYSTEMS AND METHODS FOR RECONCILING VARIANTS IN SEQUENCE DATA RELATIVE TO REFERENCE SEQUENCE DATA

(71) Applicant: Seven Bridges Genomics Inc., Cambridge, MA (US)

(72) Inventor: Amit Jain, London (GB)

(*) Notice: Subject to any disclaimer, the term of this patent is extended or adjusted under 35 U.S.C. 154(b) by 787 days.

(21) Appl. No.: 15/208,656

(22) Filed: Jul. 13, 2016

(65) Prior Publication Data

US 2018/0018423 A1    Jan. 18, 2018

(51) Int. Cl.
*G16B 30/00* (2019.01)
*G06N 7/00* (2006.01)

(52) U.S. Cl.
CPC ............ *G16B 30/00* (2019.02); *G06N 7/005* (2013.01)

(58) Field of Classification Search
None
See application file for complete search history.

(56) References Cited

U.S. PATENT DOCUMENTS

| | | | |
|---|---|---|---|
| 5,242,794 A | 9/1993 | Whiteley et al. |
| 5,701,256 A | 12/1997 | Marr et al. |
| 6,054,278 A | 4/2000 | Dodge et al. |
| 6,223,128 B1 | 4/2001 | Allex et al. |
| 6,828,100 B1 | 12/2004 | Ronaghi |
| 6,931,401 B2 | 8/2005 | Gibson et al. |
| 7,232,656 B2 | 6/2007 | Balasubramanian et al. |
| 7,809,509 B2 | 10/2010 | Milosavljevic |
| 7,917,302 B2 | 3/2011 | Rognes |
| 7,957,913 B2 | 6/2011 | Chinitz et al. |
| 7,996,157 B2 | 8/2011 | Zabeau et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,428,886 B2 | 4/2013 | Wong et al. |
| 8,725,422 B2 | 5/2014 | Halpern et al. |
| 8,775,092 B2 | 7/2014 | Colwell et al. |
| 8,880,456 B2 | 11/2014 | Kermani et al. |
| 9,063,914 B2 | 6/2015 | Kural et al. |
| 9,092,402 B2 | 7/2015 | Kural et al. |
| 9,116,866 B2 | 8/2015 | Kural |
| 9,183,349 B2 | 11/2015 | Kupershmidt et al. |
| 9,323,888 B2 | 4/2016 | Rava et al. |
| 2004/0023209 A1 | 2/2004 | Jonasson |
| 2005/0089906 A1 | 4/2005 | Furuta et al. |
| 2009/0119313 A1 | 5/2009 | Pearce |
| 2009/0233809 A1 | 9/2009 | Faham et al. |
| 2009/0318310 A1 | 12/2009 | Liu et al. |
| 2010/0169026 A1 | 7/2010 | Sorenson et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0257889 A1 | 10/2011 | Klammer et al. |
| 2012/0041727 A1 | 2/2012 | Mishra et al. |
| 2012/0239706 A1 | 9/2012 | Steinfadt et al. |
| 2012/0330566 A1 | 12/2012 | Chaisson |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0173177 A1 | 7/2013 | Pelleymounter |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0051588 A9 | 2/2014 | Drmanac et al. |
| 2014/0129201 A1 | 5/2014 | Kennedy et al. |
| 2014/0136120 A1 | 5/2014 | Colwell et al. |
| 2014/0143188 A1 | 5/2014 | Mackey et al. |
| 2014/0200147 A1 | 7/2014 | Bartha et al. |
| 2014/0280360 A1 | 9/2014 | Webber et al. |
| 2014/0336999 A1 | 11/2014 | Kumar et al. |
| 2015/0056613 A1 | 2/2015 | Kural |
| 2015/0057946 A1 | 2/2015 | Kural |
| 2015/0112602 A1 | 4/2015 | Kural et al. |
| 2015/0112658 A1 | 4/2015 | Kural et al. |

(Continued)

FOREIGN PATENT DOCUMENTS

EP    2990976 A1    3/2016
GB    2510725 B     8/2015

(Continued)

OTHER PUBLICATIONS

Kim SY, Jacob L, Speed TP. Combining calls from multiple somatic mutation-callers. BMC Bioinformatics. 2014;15: 154:8 pages.
Cantarel BL, Weaver D, McNeill N, Zhang J, Mackey AJ, Reese J. BAYSIC: a Bayesian method for combining sets of genome variants with improved specificity and sensitivity. BMC Bioinformatics. 2014;15:12 pages.
1000 Genomes Project Consortium, Abecasis GR, Altshuler D, Auton A, Brooks LD, Durbin RM, et al. A map of human genome variation from population-scale sequencing. Nature. Nature Research; 2010;467:14 pages.
1000 Genomes Project Consortium, Auton A, Brooks LD, Durbin RM, Garrison EP, Kang HM, et al. A global reference for human genetic variation. Nature. Nature Research; 2015;526: 68-74.
[No Author Listed] International HapMap Consortium. A haplotype map of the human genome. Nature. 2005;437: 1299-1320.

(Continued)

*Primary Examiner* — John S Brusca
(74) *Attorney, Agent, or Firm* — Wolf, Greenfield & Sacks, P.C.

(57) ABSTRACT

Techniques for identifying variations in sequence data relative to reference sequence data. The techniques include accessing information specifying multiple sets of variants in the sequence data relative to reference sequence data, each of the multiple sets of variants being generated by using a respective variant identification technique; and determining, using the information specifying the multiple sets of variants in the sequence data, a reconciled set of variants in the sequence data relative to the reference sequence data, the determining comprising: determining whether a first variant is present at a first position in the sequence data based, at least in part, on one or more variants at one or more other positions in the sequence data.

20 Claims, 7 Drawing Sheets

Specification includes a Sequence Listing.

(56) References Cited

U.S. PATENT DOCUMENTS

| | | | |
|---|---|---|---|
| 2016/0004817 | A1 | 1/2016 | Lawrence et al. |
| 2016/0019341 | A1 | 1/2016 | Harris et al. |
| 2016/0026757 | A1 | 1/2016 | Li et al. |
| 2016/0026760 | A1 | 1/2016 | Leong et al. |
| 2016/0085910 | A1 | 3/2016 | Bruand et al. |
| 2016/0103954 | A1 | 4/2016 | Conway et al. |
| 2016/0140289 | A1 | 5/2016 | Gibiansky et al. |
| 2016/0232291 | A1 | 8/2016 | Kyriazopoulou-Panagiotopoulou et al. |
| 2016/0283654 | A1 | 9/2016 | Ye et al. |
| 2016/0300013 | A1 | 10/2016 | Ashutosh et al. |

FOREIGN PATENT DOCUMENTS

| | | | |
|---|---|---|---|
| WO | WO 2007/030426 | A3 | 3/2007 |
| WO | WO 2012/098515 | A1 | 7/2012 |
| WO | WO 2012/096579 | A3 | 9/2012 |
| WO | WO 2012/142531 | A2 | 10/2012 |
| WO | WO 2013/040583 | A2 | 3/2013 |
| WO | WO 2013/043909 | A1 | 3/2013 |
| WO | WO 2013/106737 | A1 | 7/2013 |
| WO | WO 2013/184643 | A1 | 12/2013 |
| WO | WO 2015/027050 | A1 | 2/2015 |
| WO | WO 2015/031689 | A1 | 3/2015 |
| WO | WO 2015/058093 | A1 | 4/2015 |
| WO | WO 2015/058095 | A1 | 4/2015 |
| WO | WO 2015/112619 | A1 | 7/2015 |
| WO | WO 2015/123269 | A1 | 8/2015 |
| WO | WO 2015/123600 | A1 | 8/2015 |
| WO | WO 2015/173222 | A1 | 11/2015 |
| WO | WO 2016/040287 | A1 | 3/2016 |
| WO | WO 2016/122318 | A1 | 8/2016 |
| WO | WO 2016/138127 | A1 | 9/2016 |
| WO | WO 2016/141077 | A1 | 9/2016 |
| WO | WO 2016/154584 | A1 | 9/2016 |

OTHER PUBLICATIONS

Abouelhoda M, Issa SA, Ghanem M. Tavaxy: integrating Taverna and Galaxy workflows with cloud computing support. BMC Bioinformatics. 2012;13: 77:19 pages.
Aguiar D, Istrail S. HapCompass: a fast cycle basis algorithm for accurate haplotype assembly of sequence data. J Comput Biol. 2012;19: 577-590.
Aguiar D, Istrail S. Haplotype assembly in polyploid genomes and identical by descent shared tracts. Bioinformatics. 2013;29: i352-60.
Altschul SF, Erickson BW. Optimal sequence alignment using affine gap costs. Bull Math Biol. 1986;48: 603-616.
Aniba MR, Poch O, Thompson JD. Issues in bioinformatics benchmarking: the case study of multiple sequence alignment. Nucleic Acids Res. 2010;38: 7353-7363.
Bansal V, Halpern AL, Axelrod N, Bafna V. An MCMC algorithm for haplotype assembly from whole-genome sequence data. Genome Res. 2008;18: 1336-1346.
Bansal V, Harismendy O, Tewhey R, Murray SS, Schork NJ, Topol EJ, et al. Accurate detection and genotyping of SNPs utilizing population sequencing data. Genome Res. genome.cshlp.org; 2010;20: 537-545.
Bertrand D, Blanchette M, El-Mabrouk N. Genetic map refinement using a comparative genomic approach. J Comput Biol. 2009;16: 1475-1486.
Boyer RS, Moore JS. A fast string searching algorithm. Commun ACM. ACM; 1977;20: 762-772.
Breese MR, Liu Y. NGSUtils: a software suite for analyzing and manipulating next-generation sequencing datasets. Bioinformatics. Oxford Univ Press; 2013;29(4):494-496.
Buhler J. Search algorithms for biosequences using random projection. Doctor of Philosophy, University of Washington. 2001. 203 pages.
Challis D, Yu J, Evani US, Jackson AR, Paithankar S, Coarfa C, et al. An integrative variant analysis suite for whole exome next-generation sequencing data. BMC Bioinformatics. biomedcentral. com; 2012;13:1-12.
Chen J-M, Férec C, Cooper DN. Transient hypermutability, chromothripsis and replication-based mechanisms in the generation of concurrent clustered mutations. Mutat Res. 2012;750: 52-59.
Cheng AY, Teo Y-Y, Ong RT-H. Assessing single nucleotide variant detection and genotype calling on whole-genome sequenced individuals. Bioinformatics. 2014;30: 1707-1713.
Chuang JS, Roth D. Gene recognition based on DAG shortest paths. Bioinformatics. 2001;17 Suppl 1: S56-64.
Clark L. Illumina announces landmark $1,000 human genome sequencing. Wired. Jan. 15, 2014. Available: http://www.wired.co.uk/article/1000-dollar-genome 3 pages.
Cleary JG, Braithwaite R, Gaastra K, Hilbush BS, Inglis S, Irvine SA, et al. Joint variant and de novo mutation identification on pedigrees from high-throughput sequencing data. J Comput Biol. online.liebertpub.com; 2014;21: 405-419.
Cock PJA, Grüning BA, Paszkiewicz K, Pritchard L. Galaxy tools and workflows for sequence analysis with applications in molecular plant pathology. PeerJ. 2013;1: e167:22 pages.
Compeau PEC, Pevzner PA, Tesler G. How to apply de Bruijn graphs to genome assembly. Nat Biotechnol. 2011;29: 987-991.
Cornish A, Guda C. A Comparison of Variant Calling Pipelines Using Genome in a Bottle as a Reference. Biomed Res Int. hindawi.com; 2015;2015: 456479: 11 pages.
Craig DW, Pearson JV, Szelinger S, Sekar A, Redman M, Corneveaux JJ, et al. Identification of genetic variants using barcoded multiplexed sequencing. Nat Methods. 2008;5(10):16 pages.
Danecek P, Auton A, Abecasis G, Albers CA, Banks E, DePristo MA, et al. The variant call format and VCFtools. Bioinformatics. 2011;27: 2156-2158.
David W. Mount. Multiple Sequence Alignment. In: Cuddihy J, Barker P, editors. Bioinformatics: Sequence and Genome Analysis. Cold Spring Harbor Laboratory Press; 2001. 68 pages.
Davies KD, Farooqi MS, Gruidl M, Hill CE, Woolworth-Hirschhorn J, Jones H, et al. Multi-Institutional FASTQ File Exchange as a Means of Proficiency Testing for Next-Generation Sequencing Bioinformatics and Variant Interpretation. J Mol Diagn. Elsevier; 2016;18: 572-579.
Delcher AL, Kasif S, Fleischmann RD, Peterson J, White O, Salzberg SL. Alignment of whole genomes. Nucleic Acids Res. 1999;27: 2369-2376.
DePristo MA, Banks E, Poplin R, Garimella KV, Maguire JR, Hartl C, et al. A framework for variation discovery and genotyping using next-generation DNA sequencing data. Nat Genet. 2011;43: 19 pages.
Dolled-Filhart MP, Lee M Jr, Ou-Yang C-W, Haraksingh RR, Lin JC-H. Computational and bioinformatics frameworks for next-generation whole exome and genome sequencing. ScientificWorldJournal. hindawi.com; 2013;2013: 10 pages.
Edmonson MN, Zhang J, Yan C, Finney RP, Meerzaman DM, Buetow KH. Bambino: a variant detector and alignment viewer for next-generation sequencing data in the SAM/BAM format. Bioinformatics. Oxford Univ Press; 2011;27: 865-866.
Endelman JB. New algorithm improves fine structure of the barley consensus SNP map. BMC Genomics. 2011;12: 9 pages.
Farrar M. Striped Smith-Waterman speeds database searches six times over other SIMD implementations. Bioinformatics. 2007;23: 156-161.
Farrer RA, Henk DA, MacLean D, Studholme DJ, Fisher MC. Using false discovery rates to benchmark SNP-callers in next-generation sequencing projects. Sci Rep. nature.com; 2013;3:1-6.
Flicek P, Birney E. Sense from sequence reads: methods for alignment and assembly. Nat Methods. 2009;6: S6-S12.
Garrison E, Marth G. Haplotype-based variant detection from short-read sequencing. arXiv. 1207.3907. Jul. 24, 2012:1-9.
Ghoneim DH, Myers JR, Tuttle E, Paciorkowski AR. Comparison of insertion/deletion calling algorithms on human next-generation sequencing data. BMC Res Notes. 2014;7:1-10.

(56) References Cited

OTHER PUBLICATIONS

Giannoulatou E, Yau C, Colella S, Ragoussis J, Holmes CC. GenoSNP: a variational Bayes within-sample SNP genotyping algorithm that does not require a reference population. Bioinformatics. 2008;24: 2209-2214.
Giegerich R. A systematic approach to dynamic programming in bioinformatics. Bioinformatics. Oxford Univ Press; 2000;16: 665-677.
Glusman G, Cox HC, Roach JC. Whole-genome haplotyping approaches and genomic medicine. Genome Med. 2014;6:1-16.
Gotoh O. An improved algorithm for matching biological sequences. J Mol Biol. 1982;162: 705-708.
Gotoh O. Multiple sequence alignment: algorithms and applications. Adv Biophys. 1999;36: 159-206.
Grasso C, Lee C. Combining partial order alignment and progressive multiple sequence alignment increases alignment speed and scalability to very large alignment problems. Bioinformatics. 2004;20(10): 1546-1556.
Haas BJ, Delcher AL, Wortman JR, Salzberg SL. DAGchainer: a tool for mining segmental genome duplications and synteny. Bioinformatics. 2004;20: 3643-3646.
Hamada M, Wijaya E, Frith MC, Asai K. Probabilistic alignments with quality scores: an application to short-read mapping toward accurate SNP/indel detection. Bioinformatics. Oxford Univ Press; 2011;27: 3085-3092.
Hansen NF. Variant Calling From Next Generation Sequence Data. In: Mathé E, Davis S, editors. Statistical Genomics. New York, NY: Springer New York; 2016. pp. 209-224.
He D, Choi A, Pipatsrisawat K, Darwiche A, Eskin E. Optimal algorithms for haplotype assembly from whole-genome sequence data. Bioinformatics. 2010;26: i183-90.
Hein J. A new method that simultaneously aligns and reconstructs ancestral sequences for any number of homologous sequences, when the phylogeny is given. Mol Biol Evol. 1989;6: 649-668.
Highnam G, Wang JJ, Kusler D, Zook J, Vijayan V, Leibovich N, et al. An analytical framework for optimizing variant discovery from personal genomes. Nat Commun. 2015;6:1-6.
Homer N, Merriman B, Nelson SF. BFAST: an alignment tool for large scale genome resequencing. PLoS One. 2009;4: e7767:1-12.
Homer N, Nelson SF. Improved variant discovery through local re-alignment of short-read next-generation sequencing data using SRMA. Genome Biol. 2010;11: 1-12.
Horspool RN. Practical fast searching in strings. Softw Pract Exp. John Wiley & Sons, Ltd.; 1980;10: 501-506.
Huang X. Bio-sequence Comparison and Applications. In: Jiang T, Xu Y, Zhang MQ, editors. Current Topics in Computational Molecular Biology. MIT Press; 2002. 29 pages.
Hutchinson JN, Raj T, Fagerness J, Stahl E, Viloria FT, Gimelbrant A, et al. Allele-specific methylation occurs at genetic variants associated with complex disease. PLoS One. 2014;9: e98464:1-14.
Hwang S, Kim E, Lee I, Marcotte EM. Systematic comparison of variant calling pipelines using gold standard personal exome variants. Sci Rep. 2015;5: 17875:1-8.
Ji HP. Improving bioinformatic pipelines for exome variant calling. Genome Med. 2012;4:7:1-4.
Katoh K, Kuma K-I, Toh H, Miyata T. MAFFT version 5: improvement in accuracy of multiple sequence alignment. Nucleic Acids Res. 2005;33: 511-518.
Kehr B, Trappe K, Holtgrewe M, Reinert K. Genome alignment with graph data structures: a comparison. BMC Bioinformatics. 2014;15(99):20 pages.
Kent WJ. BLAT—The BLAST-Like Alignment Tool. Genome Res. 2002;12: 656-664.
Kim D, Pertea G, Trapnell C, Pimentel H, Kelley R, Salzberg SL. TopHat2: accurate alignment of transcriptomes in the presence of insertions, deletions and gene fusions. Genome Biol. 2013;14: R36:13 pages.
Kim P-G, Cho H-G, Park K. A scaffold analysis tool using mate-pair information in genome sequencing. J Biomed Biotechnol. 2008;2008: 675741:7 pages.
Kim SY, Speed TP. Comparing somatic mutation-callers: beyond Venn diagrams. BMC Bioinformatics. 2013;14: 189:16 pages.
Koboldt DC, Larson DE, Wilson RK. Using VarScan 2 for Germline Variant Calling and Somatic Mutation Detection. Curr Protoc Bioinformatics. Wiley Online Library; 2013;44: 15.4. 22 pages.
Korbel JO, Abyzov A, Mu XJ, Carriero N, Cayting P, Zhang Z, et al. PEMer: a computational framework with simulation-based error models for inferring genomic structural variants from massive paired-end sequencing data. Genome Biol. genomebiology.biomedcentral.com; 2009;10: R23-R23.14.
Kosugi S, Natsume S, Yoshida K, MacLean D, Cano L, Kamoun S, et al. Coval: improving alignment quality and variant calling accuracy for next-generation sequencing data. PLoS One. journals.plos.org; 2013;8: e75402:1-11.
Krishnan V, Zia A, Utiramerur S, Datta S. Benchmarking variant callers: Towards building a robust exome pipeline [Internet]. med.stanford.edu; 2016. Available: http://med.stanford.edu/content/dam/sm/gbsc/GeneticsRetreatPosterSep2016-VK.pdf 1 page.
Kumar P, Al-Shafai M, Al Muftah WA, Chalhoub N, Elsaid MF, Aleem AA, et al. Evaluation of SNP calling using single and multiple-sample calling algorithms by validation against array base genotyping and Mendelian inheritance. BMC Res Notes. bmcresnotes.biomedcentral.com; 2014;7: 747:1-13.
Kurtz S, Phillippy A, Delcher AL, Smoot M, Shumway M, Antonescu C, et al. Versatile and open software for comparing large genomes. Genome Biol. 2004;5: R12. 9 pages.
LaFramboise T. Single nucleotide polymorphism arrays: a decade of biological, computational and technological advances. Nucleic Acids Res. 2009;37: 4181-4193.
Lai Z, Markovets A, Ahdesmaki M, Chapman B, Hofmann O, McEwen R, et al. VarDict: a novel and versatile variant caller for next-generation sequencing in cancer research. Nucleic Acids Res. 2016;44: e108:1-11.
Lam HYK, Clark MJ, Chen R, Chen R, Natsoulis G, O'Huallachain M, et al. Performance comparison of whole-genome sequencing platforms. Nat Biotechnol. nature.com; 2011;30: 1-16.
Lam HYK, Pan C, Clark MJ, Lacroute P, Chen R, Haraksingh R, et al. Detecting and annotating genetic variations using the HugeSeq pipeline. Nat Biotechnol. nature.com; 2012;30: 1-9.
Lam TW, Sung WK, Tam SL, Wong CK, Yiu SM. Compressed indexing and local alignment of DNA. Bioinformatics. 2008;24: 791-797.
Langmead B, Salzberg SL. Fast gapped-read alignment with Bowtie 2. Nat Methods. nature.com; 2012;9: 1-8.
Langmead B, Trapnell C, Pop M, Salzberg SL. Ultrafast and memory-efficient alignment of short DNA sequences to the human genome. Genome Biol. 2009;10: R25-R25.10.
Larkin MA, Blackshields G, Brown NP, Chenna R, McGettigan PA, McWilliam H, et al. Clustal W and Clustal X version 2.0. Bioinformatics. 2007;23: 2947-2948.
Layer RM, Chiang C, Quinlan AR, Hall IM. LUMPY: a probabilistic framework for structural variant discovery. Genome Biol. genomebiology.biomedcentral.com; 2014;15: R84:19 pages.
Lee C, Grasso C, Sharlow MF. Multiple sequence alignment using partial order graphs. Bioinformatics. 2002;18: 452-464.
Lee C. Generating consensus sequences from partial order multiple sequence alignment graphs. Bioinformatics. 2003;19: 999-1008.
Lee HC, Lai K, Lorenc MT, Imelfort M, Duran C, Edwards D. Bioinformatics tools and databases for analysis of next-generation sequence data. Brief Funct Genomics. bfg.oxfordjournals.org; 2012;11: 12-24.
Lee W-P, Stromberg MP, Ward A, Stewart C, Garrison EP, Marth GT. MOSAIK: a hash-based algorithm for accurate next-generation sequencing short-read mapping. PLoS One. 2014;9: e90581:1-11.
Li B, Chen W, Zhan X, Busonero F, Sanna S, Sidore C, et al. A likelihood-based framework for variant calling and de novo mutation detection in families. PLoS Genet. journals.plos.org; 2012;8: e1002944:1-12.
Li H, Durbin R. Fast and accurate short read alignment with Burrows-Wheeler transform. Bioinformatics. 2009;25: 1754-1760.
Li H, Handsaker B, Wysoker A, Fennell T, Ruan J, Homer N, et al. The Sequence Alignment/Map format and SAMtools. Bioinformatics. 2009;25: 2078-2079.

(56) References Cited

OTHER PUBLICATIONS

Li H, Homer N. A survey of sequence alignment algorithms for next-generation sequencing. Brief Bioinform. 2010;11: 473-483.
Li H, Ruan J, Durbin R. Mapping short DNA sequencing reads and calling variants using mapping quality scores. Genome Res. genome.cshlp.org; 2008;18: 1851-1858.
Li H. A statistical framework for SNP calling, mutation discovery, association mapping and population genetical parameter estimation from sequencing data. Bioinformatics. Oxford Univ Press; 2011;27: 2987-2993.
Li H. Exploring single-sample SNP and INDEL calling with whole-genome de novo assembly. Bioinformatics. 2012;28: 1838-1844.
Li H. Toward better understanding of artifacts in variant calling from high-coverage samples. Bioinformatics. 2014;30: 2843-2851.
Li R, Li Y, Kristiansen K, Wang J. SOAP: short oligonucleotide alignment program. Bioinformatics. 2008;24: 713-714.
Li R, Yu C, Li Y, Lam T-W, Yiu S-M, Kristiansen K, et al. SOAP2: an improved ultrafast tool for short read alignment. Bioinformatics. 2009;25: 1966-1967.
Li Y, Chen W, Liu EY, Zhou Y-H. Single Nucleotide Polymorphism (SNP) Detection and Genotype Calling from Massively Parallel Sequencing (MPS) Data. Stat Biosci. Springer; 2013;5: 26 pages.
Lin S, Carvalho B, Cutler DJ, Arking DE, Chakravarti A, Irizarry RA. Validation and extension of an empirical Bayes method for SNP calling on Affymetrix microarrays. Genome Biol. 2008;9: R63-R63.12.
Liu X, Han S, Wang Z, Gelernter J, Yang B-Z. Variant callers for next-generation sequencing data: a comparison study. PLoS One. journals.plos.org; 2013;8: e75619:1-11.
Lücking R, Hodkinson BP, Stamatakis A, Cartwright RA. PICS-Ord: unlimited coding of ambiguous regions by pairwise identity and cost scores ordination. BMC Bioinformatics. 2011;12: 1-15.
Ma F, Deogun JS. Multiple genome alignment based on longest path in directed acyclic graphs. IJBRA. 2010;6: 366.
Manolio TA. Genomewide association studies and assessment of the risk of disease. N Engl J Med. 2010;363: 166-176.
Martin ER, Kinnamon DD, Schmidt MA, Powell EH, Zuchner S, Morris RW. SeqEM: an adaptive genotype-calling approach for next-generation sequencing studies. Bioinformatics. Oxford Univ Press; 2010;26: 2803-2810.
Mazrouee S, Wang W. FastHap: fast and accurate single individual haplotype reconstruction using fuzzy conflict graphs. Bioinformatics. 2014;30: i371-8.
McKenna A, Hanna M, Banks E, Sivachenko A, Cibulskis K, Kernytsky A, et al. The Genome Analysis Toolkit: a MapReduce framework for analyzing next-generation DNA sequencing data. Genome Res. 2010;20: 1297-1303.
Miller JR, Koren S, Sutton G. Assembly algorithms for next-generation sequencing data. Genomics. 2010;95: 31 pages.
Misra S, Agrawal A, Liao W-K, Choudhary A. Anatomy of a hash-based long read sequence mapping algorithm for next generation DNA sequencing. Bioinformatics. 2011;27: 189-195.
Mohiyuddin M, Mu JC, Li J, Bani Asadi N, Gerstein MB, Abyzov A, et al. MetaSV: an accurate and integrative structural-variant caller for next generation sequencing. Bioinformatics. Oxford Univ Press; 2015;31: 2741-2744.
Mu JC, Tootoonchi Afshar P, Mohiyuddin M, Chen X, Li J, Bani Asadi N, et al. Leveraging long read sequencing from a single individual to provide a comprehensive resource for benchmarking variant calling methods. Sci Rep. 2015;5: 14493:1-6.
Nagarajan N, Pop M. Sequence assembly demystified. Nat Rev Genet. Nature Publishing Group; 2013;14: 157-167.
Najafi A, Nashta-ali D, Motahari SA, Khani M, Khalaj BH, Rabiee HR. Fundamental Limits of Pooled-DNA Sequencing. 2016. 38 pages.
Needleman SB, Wunsch CD. A general method applicable to the search for similarities in the amino acid sequence of two proteins. J Mol Biol. 1970;48: 443-453.
Nekrutenko A, Taylor J. Next-generation sequencing data interpretation: enhancing reproducibility and accessibility. Nat Rev Genet. nature.com; 2012;13: 667-672.
Nielsen R, Korneliussen T, Albrechtsen A, Li Y, Wang J. SNP calling, genotype calling, and sample allele frequency estimation from New-Generation Sequencing data. PLoS One. journals.plos.org; 2012;7: e37558:1-11.
Nielsen R, Paul JS, Albrechtsen A, Song YS. Genotype and SNP calling from next-generation sequencing data. Nat Rev Genet. Nature Publishing Group; 2011;12: 443-451.
Ning Z, Cox AJ, Mullikin JC. SSAHA: a fast search method for large DNA databases. Genome Res. 2001;11: 1725-1729.
O'Fallon BD, Wooderchak-Donahue W, Crockett DK. A support vector machine for identification of single-nucleotide polymorphisms from next-generation sequencing data. Bioinformatics. 2013;29: 1361-1366.
O'Rawe J, Jiang T, Sun G, Wu Y, Wang W, Hu J, et al. Low concordance of multiple variant-calling pipelines: practical implications for exome and genome sequencing. Genome Med. 2013;5: 28:1-18.
O'Rawe JA, Ferson S, Lyon GJ. Accounting for uncertainty in DNA sequencing data. Trends Genet. Elsevier; 2015;31: 61-66.
Pabinger S, Dander A, Fischer M, Snajder R, Sperk M, Efremova M, et al. A survey of tools for variant analysis of next-generation genome sequencing data. Brief Bioinform. Oxford University Press; 2014;15: 256-278.
Pe'er I, de Bakker PIW, Mailer J, Yelensky R, Altshuler D, Daly MJ. Evaluating and improving power in whole-genome association studies using fixed marker sets. Nat Genet. 2006;38: 663-667.
Pearson WR, Lipman DJ. Improved tools for biological sequence comparison. Proc Natl Acad Sci U S A. 1988;85: 2444-2448.
Pirooznia M, Kramer M, Parla J, Goes FS, Potash JB, McCombie WR, et al. Validation and assessment of variant calling pipelines for next-generation sequencing. Hum Genomics. 2014;8: 14:1-10.
Pope BJ, Nguyen-Dumont T, Hammet F, Park DJ. ROVER variant caller: read-pair overlap considerate variant-calling software applied to PCR-based massively parallel sequencing datasets. Source Code Biol Med. 2014;9: 3:1-5.
Porter J, Berkhahn J, Zhang L. A Comparative Analysis of Computational Indel Calling Pipelines for Next Generation Sequencing Data. Proceedings of the International Conference on Bioinformatics & Computational Biology (BIOCOMP). The Steering Committee of The World Congress in Computer Science, Computer Engineering and Applied Computing (WorldComp); 2014. 6 pages.
Quail MA, Smith M, Coupland P, Otto TD, Harris SR, Connor TR, et al. A tale of three next generation sequencing platforms: comparison of Ion Torrent, Pacific Biosciences and Illumina MiSeq sequencers. BMC Genomics. 2012;13: 341:1-13.
Raphael B, Zhi D, Tang H, Pevzner P. A novel method for multiple alignment of sequences with repeated and shuffled elements. Genome Res. 2004;14: 2336-2346.
Rausch T, Zichner T, Schlattl A, Stütz AM, Benes V, Korbel JO. DELLY: structural variant discovery by integrated paired-end and split-read analysis. Bioinformatics. Oxford Univ Press; 2012;28: i333-i339.
Reumers J, De Rijk P, Zhao H, Liekens A, Smeets D, Cleary J, et al. Optimized filtering reduces the error rate in detecting genomic variants by short-read sequencing. Nat Biotechnol. nature.com; 2011;30: 10 pages.
Rieber N, Zapatka M, Lasitschka B, Jones D, Northcott P, Hutter B, et al. Coverage bias and sensitivity of variant calling for four whole-genome sequencing technologies. PLoS One. journals.plos.org; 2013;8: e66621:11 pages.
Rimmer A, Phan H, Mathieson I, Iqbal Z, Twigg SRF, WGS500 Consortium, et al. Integrating mapping-, assembly- and haplotype-based approaches for calling variants in clinical sequencing applications. Nat Genet. 2014;46: 9 pages.
Robertson G, Schein J, Chiu R, Corbett R, Field M, Jackman SD, et al. De novo assembly and analysis of RNA-seq data. Nat Methods. 2010;7: 7 pages.

(56) References Cited

OTHER PUBLICATIONS

Ronquist F, Teslenko M, van der Mark P, Ayres DL, Darling A, Höhna S, et al. MrBayes 3.2: efficient Bayesian phylogenetic inference and model choice across a large model space. Syst Biol. 2012;61: 539-542.
Rothberg JM, Hinz W, Rearick TM, Schultz J, Mileski W, Davey M, et al. An integrated semiconductor device enabling non-optical genome sequencing. Nature. 2011;475: 348-352.
Ruffalo M, LaFramboise T, Koyuttirk M. Comparative analysis of algorithms for next-generation sequencing read alignment. Bioinformatics. Oxford Univ Press; 2011;27: 2790-2796.
San Lucas FA, Wang G, Scheet P, Peng B. Integrated annotation and analysis of genetic variants from next-generation sequencing studies with variant tools. Bioinformatics. Oxford Univ Press; 2012;28: 421-422.
Sato K, Mituyama T, Asai K, Sakakibara Y. Directed acyclic graph kernels for structural RNA analysis. BMC Bioinformatics. 2008;9: 318:12 pages.
Saunders CT, Wong WSW, Swamy S, Becq J, Murray LJ, Cheetham RK. Strelka: accurate somatic small-variant calling from sequenced tumor-normal sample pairs. Bioinformatics. Oxford Univ Press; 2012;28: 1811-1817.
Schneeberger K, Hagmann J, Ossowski S, Warthmann N, Gesing S, Kohlbacher O, et al. Simultaneous alignment of short reads against multiple genomes. Genome Biol. 2009;10: R98.1-R98.12.
Schwikowski B, Vingron M. Weighted sequence graphs: boosting iterated dynamic programming using locally suboptimal solutions. Discrete Appl Math. 2003;127: 95-117.
Shen Y, Wan Z, Coarfa C, Drabek R, Chen L, Ostrowski EA, et al. A SNP discovery method to assess variant allele probability from next-generation resequencing data. Genome Res. genome.cshlp.org; 2010;20: 273-280.
Shendure J, Ji H. Next-generation DNA sequencing. Nat Biotechnol. 2008;26: 1135-1145.
Slater GSC, Birney E. Automated generation of heuristics for biological sequence comparison. BMC Bioinformatics. 2005;6: 31:11 pages.
Smith TF, Waterman MS. Identification of common molecular subsequences. J Mol Biol. 1981;147: 4 pages.
Soni GV, Meller A. Progress toward ultrafast DNA sequencing using solid-state nanopores. Clin Chem. 2007;53: 1996-2001.
Sosa MX, Sivakumar IKA, Maragh S, Veeramachaneni V, Hariharan R, Parulekar M, et al. Next-generation sequencing of human mitochondrial reference genomes uncovers high heteroplasmy frequency. PLoS Comput Biol. 2012;8: e1002737:1-11.
Spencer DH, Tyagi M, Vallania F, Bredemeyer AJ, Pfeifer JD, Mitra RD, et al. Performance of common analysis methods for detecting low-frequency single nucleotide variants in targeted next-generation sequence data. J Mol Diagn. Elsevier; 2014;16: 75-88.
Stephens M, Smith NJ, Donnelly P. A new statistical method for haplotype reconstruction from population data. Am J Hum Genet. 2001;68: 978-989.
Stewart C, Kural D, Strömberg MP, Walker JA, Konkel MK, Stütz AM, et al. A comprehensive map of mobile element insertion polymorphisms in humans. PLoS Genet. 2011;7: e1002236:1-19.
Szalkowski AM, Anisimova M. Graph-based modeling of tandem repeats improves global multiple sequence alignment. Nucleic Acids Res. 2013;41: e162:1-11.
Szalkowski AM. Fast and robust multiple sequence alignment with phylogeny-aware gap placement. BMC Bioinformatics. 2012;13: 129:1-11.
Talwalkar A, Liptrap J, Newcomb J, Hartl C, Terhorst J, Curtis K, et al. SMaSH: a benchmarking toolkit for human genome variant calling. Bioinformatics. Oxford Univ Press; 2014;30: 2787-2795.
Tan A, Abecasis GR, Kang HM. Unified representation of genetic variants. Bioinformatics. Oxford Univ Press; 2015;31: 2202-2204.
Thomas UG. Community-wide Effort Aims to Better Represent Variation in Human Reference Genome. GenomeWeb. Dec. 18, 2014. https://www.genomeweb.com/informatics/community-wide-effort-aims-better-represent-variation-human-reference-genome 11 pages.
Tian S, Yan H, Kalmbach M, Slager SL. Impact of post-alignment processing in variant discovery from whole exome data. BMC Bioinformatics. 2016;17: 403:1-13.
Torri F, Dinov ID, Zamanyan A, Hobel S, Genco A, Petrosyan P, et al. Next generation sequence analysis and computational genomics using graphical pipeline workflows. Genes. 2012;3: 185 pages.
Vallania FLM, Druley TE, Ramos E, Wang J, Borecki I, Province M, et al. High-throughput discovery of rare insertions and deletions in large cohorts. Genome Res. 2010;20: 1711-1718.
Van der Auwera GA, Carneiro MO, Hartl C, Poplin R, Del Angel G, Levy-Moonshine A, et al. From FastQ data to high confidence variant calls: the Genome Analysis Toolkit best practices pipeline. Curr Protoc Bioinformatics. Wiley Online Library; 2013;43: 11.10. 1-43.
Vergara IA, Frech C, Chen N. CooVar: co-occurring variant analyzer. BMC Res Notes. bmcresnotes.biomedcentral.com; 2012;5: 615:1-7.
Wallace IM, Blackshields G, Higgins DG. Multiple sequence alignments. Curr Opin Struct Biol. 2005;15: 261-266.
Wang W, Wei Z, Lam T-W, Wang J. Next generation sequencing has lower sequence coverage and poorer SNP-detection capability in the regulatory regions. Sci Rep. 2011;1: 55:1-7.
Wang Y, Lu J, Yu J, Gibbs RA, Yu F. An integrative variant analysis pipeline for accurate genotype/haplotype inference in population NGS data. Genome Res. genome.cshlp.org; 2013;23: 833-842.
Warden CD, Adamson AW, Neuhausen SL, Wu X. Detailed comparison of two popular variant calling packages for exome and targeted exon studies. PeerJ. peerj.com; 2014;2: e600:1-27.
Waterman MS, Smith TF, Beyer WA. Some biological sequence metrics. Adv Math. 1976;20: 367-387.
Wei Z, Wang W, Hu P, Lyon GJ, Hakonarson H. SNVer: a statistical tool for variant calling in analysis of pooled or individual next-generation sequencing data. Nucleic Acids Res. Oxford Univ Press; 2011;39: e132:1-13.
Wilm A, Aw PPK, Bertrand D, Yeo GHT, Ong SH, Wong CH, et al. LoFreq: a sequence-quality aware, ultra-sensitive variant caller for uncovering cell-population heterogeneity from high-throughput sequencing datasets. Nucleic Acids Res. Oxford Univ Press; 2012;40: 11189-11201.
Wu TD, Nacu S. Fast and SNP-tolerant detection of complex variants and splicing in short reads. Bioinformatics. 2010;26: 873-881.
Yang W-Y, Hormozdiari F, Wang Z, He D, Pasaniuc B, Eskin E. Leveraging reads that span multiple single nucleotide polymorphisms for haplotype inference from sequencing data. Bioinformatics. 2013;29: 2245-2252.
Yanovsky V, Rumble SM, Brudno M. Read Mapping Algorithms for Single Molecule Sequencing Data. In: Crandall KA, Lagergren J, editors. Algorithms in Bioinformatics. Berlin, Heidelberg: Springer Berlin Heidelberg; 2008. 12 pages.
Yau C, Papaspiliopoulos O, Roberts GO, Holmes C. Bayesian Nonparametric Hidden Markov Models with application to the analysis of copy-number-variation in mammalian genomes. J R Stat Soc Series B Stat Methodol. Wiley Online Library; 2011;73: 24 pages.
You N, Murillo G, Su X, Zeng X, Xu J, Ning K, et al. SNP calling using genotype model selection on high-throughput sequencing data. Bioinformatics. Oxford Univ Press; 2012;28: 643-650.
Yu X, Sun S. Comparing a few SNP calling algorithms using low-coverage sequencing data. BMC Bioinformatics. 2013;14: 274:15 pages.
Zhang K, Qin Z, Chen T, Liu JS, Waterman MS, Sun F. HapBlock: haplotype block partitioning and tag SNP selection software using a set of dynamic programming algorithms. Bioinformatics. Oxford Univ Press; 2005;21: 131-134.
Zhang P, Tan G, Gao GR. Implementation of the Smith-Waterman algorithm on a reconfigurable supercomputing platform. Proceedings of the 1st international workshop on High-performance reconfigurable computing technology and applications: held in conjunction with SC07. ACM; 2007. 18 pages.

(56) References Cited

OTHER PUBLICATIONS

Zhao Z, Wang W, Wei Z. An empirical Bayes testing procedure for detecting variants in analysis of next generation sequencing data. Ann Appl Stat. Institute of Mathematical Statistics; 2013;7: 20 pages.

Zook JM, Chapman B, Wang J, Mittelman D, Hofmann O, Hide W, et al. Integrating human sequence data sets provides a resource of benchmark SNP and indel genotype calls. Nat Biotechnol. 2014;32: 8 pages.

SYSTEMS AND METHODS FOR RECONCILING VARIANTS IN SEQUENCE DATA RELATIVE TO REFERENCE SEQUENCE DATA

FIELD

Aspects of the technology described herein relate to analysis of genetic sequence data to identify variants in the sequence data relative to reference genetic sequence data.

BACKGROUND

Advances in sequencing technology, including the development of next generation DNA sequencing methods, have made sequencing an important tool used both in research and in medicine. Some applications of sequencing technology include aligning the sequence data obtained by sequencing techniques against reference sequence data, and identifying the differences, sometimes termed "variants," between the sequence data and the reference sequence data. In turn, the identified differences may be used for diagnostic, therapeutic, research, and/or other purposes.

A variant identification technique, sometimes referred to herein as a "variant caller," is a technique for identifying differences between sequence data and the reference sequence data to which the sequence data may be aligned. A variant identification technique may identify one or multiple types of variants such as, for example, a single nucleotide polymorphism or SNP (e.g., where a single nucleotide in the sequence data differs from a corresponding nucleotide in the reference sequence data to which it is aligned), an insertion (e.g., where the sequence data includes one or more nucleotides not present in the reference sequence data to which it is aligned), and a deletion (e.g., where the sequence data does not include one or more nucleotides present in the reference sequence to which it is aligned). Multiple different variant identification techniques are used including the Genome Analysis Tool Kit HaplotypeCaller (GATK-HC), GATK UnifiedGenotyper, SAMtools mpileup, FreeBayes, Ion Proton Variant Caller, SNPSVM, and Atlas 2. These variant callers differ in their approach to identifying variants.

A variant identification technique may identify one or more variants incorrectly. An incorrect variant call may be due to one or multiple sources of error including, but not limited to, errors in sample processing (e.g., errors due to DNA polymerase infidelity during replication), errors in sequencing (which may be random or systematic in nature), and errors associated with aligning the sequence data (e.g., sequence reads obtained by sequencing a sample) to reference sequence data (e.g., a reference genome). As such, some differences between sequence data and reference sequences data may result from one or multiple errors occurring during the process of obtaining the sequence data from a genetic sample and aligning the obtained sequence to the reference sequence data, and, therefore, may not be actual differences between the nucleotide sequence in the genetic sample and the reference sequence data.

SUMMARY

Some embodiments are directed to a system for identifying variations in sequence data relative to reference sequence data. The system comprises at least one computer hardware processor; and at least one non-transitory computer-readable storage medium storing processor-executable instructions that, when executed by the at least one computer hardware processor, cause the at least one computer hardware processor to perform: accessing information specifying multiple sets of variants in the sequence data relative to reference sequence data, each of the multiple sets of variants being generated by using a respective variant identification technique; and determining, using the information specifying the multiple sets of variants in the sequence data, a reconciled set of variants in the sequence data relative to the reference sequence data. The determining comprises determining whether a first variant is present at a first position in the sequence data based, at least in part, on one or more variants at one or more other positions in the sequence data.

Some embodiments are directed to a method for identifying variations in sequence data relative to reference sequence data. The method comprises using at least one computer hardware processor to perform: accessing information specifying multiple sets of variants in the sequence data relative to the reference sequence data, each of the multiple sets of variants being generated by using a respective variant identification technique; and determining, using the information specifying the multiple sets of variants in the sequence data, a reconciled set of variants in the sequence data relative to the reference sequence data. The determining comprises determining whether a first variant is present at a first position in the sequence data based, at least in part, on one or more variants at one or more other positions in the sequence data.

Some embodiments are directed to at least one non-transitory computer-readable storage medium storing processor-executable instructions that, when executed by at least one computer hardware processor, cause the at least one computer hardware processor to perform: accessing information specifying multiple sets of variants in sequence data relative to reference sequence data, each of the multiple sets of variants being generated by using a respective variant identification technique; and determining, using the information specifying the multiple sets of variants in the sequence data, a reconciled set of variants in the sequence data relative to the reference sequence data. The determining comprises determining whether a first variant is present at a first position in the sequence data based, at least in part, on one or more variants at one or more other positions in the sequence data.

BRIEF DESCRIPTION OF DRAWINGS

Various aspects and embodiments will be described with reference to the following figures. The figures are not necessarily drawn to scale.

FIG. 5B is a diagram of an illustrative graph of variant calls, in accordance with some embodiments of the technology described herein. This figure depicts SEQ ID NO: 1.

FIG. 5C shows the illustrative graph of variant calls of FIG. 5B together with scores assigned to the nodes of the graph, in accordance with some embodiments of the technology described herein. This figure includes SEQ ID NO: 1.

FIG. 5D shows a minimum cost path, identified in the graph of variant calls of FIG. 5B, indicating a reconciled set of variant calls, in accordance with some embodiments of the technology described herein.

DETAILED DESCRIPTION

Figure 1:
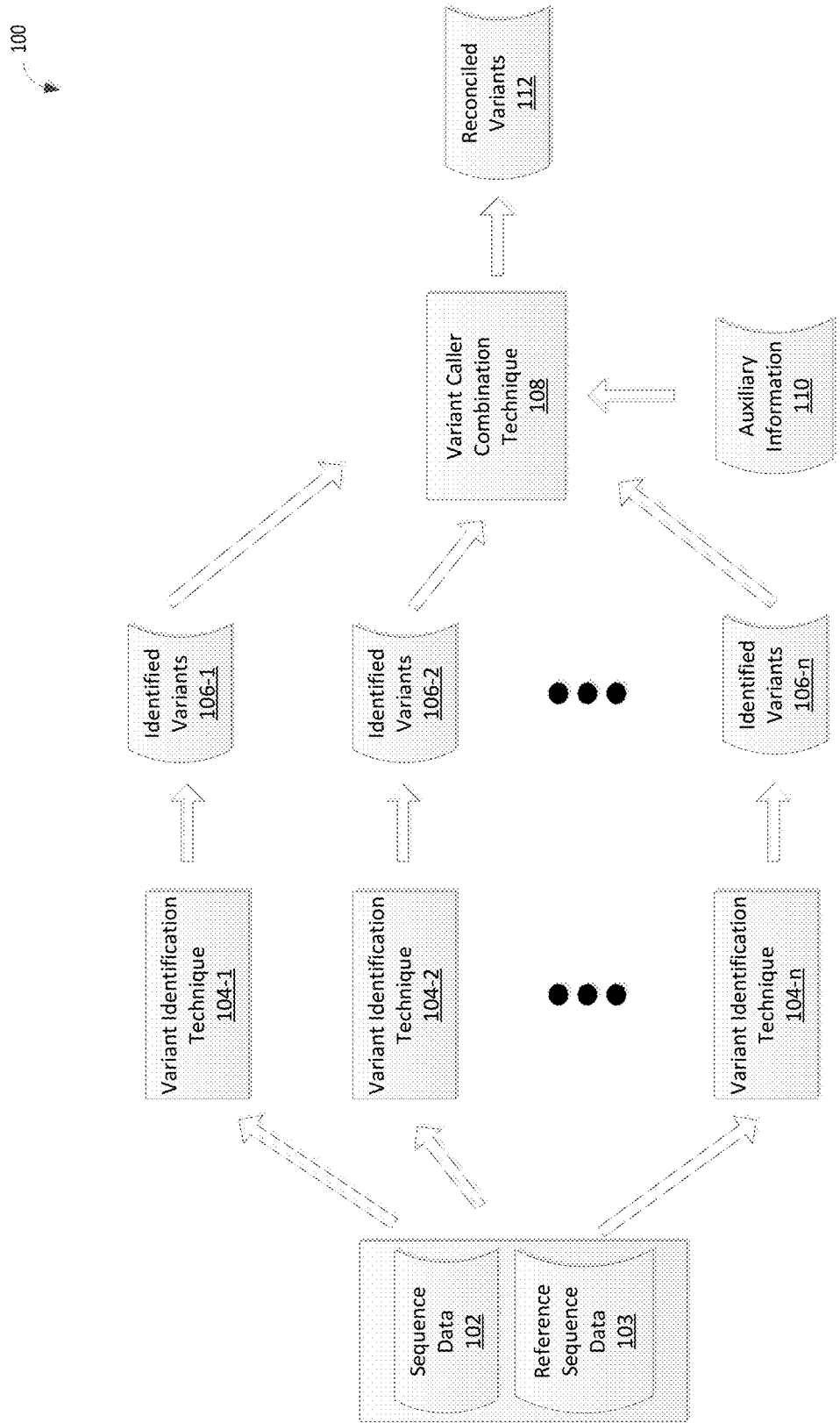
FIG. 1 is a diagram of an illustrative data processing pipeline for identifying a set of variants in sequence data relative to reference sequence data by using multiple variant identification techniques, in accordance with some embodiments of the technology described herein.

The inventors have appreciated that conventional variant identification techniques may be improved upon. Applying different conventional variant identification techniques to the same sequence data may produce different and inconsistent results. For example, different variant callers may identify different variants at the same position in the sequence data. As another example, one variant caller may detect the presence of a variant at a position, but another variant caller may not identify any variant at that position. On the other hand, there is no single variant identification technique that is universally preferred over others by practitioners, as some variant identification techniques are better at identifying one type of variant (e.g., SNPs) while other variant identification techniques are better at identifying another type of variant (e.g., insertions and deletions). Consequently, a person (e.g., a researcher, a scientist, a doctor, etc.) wishing to identify variants in sequence data either has to use a single variant identification technique, which may not be the best technique for identifying all types of variants, or use multiple variant identification techniques, which may provide different and inconsistent results. The inventors have appreciated that neither of these options is appealing.

Accordingly, the inventors have developed techniques for combining multiple sets of variants identified by different variant identification techniques (i.e., "variant calls," or "called variants") to obtain a "best effort" list of variants in the sequence data relative to reference sequence data. These developed techniques, which are described herein, reconcile any differences and/or inconsistencies among the variants identified by multiple variant callers to produce a single reconciled set of variants in the sequence data relative to the reference sequence data.

Although attempts have been made at combining output of multiple variant callers, these approaches were either manual (which is expensive, time-intensive, and does not scale) or myopic in the sense that results generated by multiple variant callers were combined at a particular position in the sequence data without taking into account variants identified at one or more other positions in the sequence data by any of the variant callers. For example, one conventional myopic approach to combining variant calls from multiple variant callers is to use a voting scheme by which a variant is determined to occur at a particular position in the sequence data based solely on whether a majority of the multiple variant callers have identified this variant at this particular position. The votes of the multiple variant callers may be weighted equally or not, but a combined call at the particular position does not depend on the variants identified by any of the variant callers (whose results are being combined) at any other position. By contrast, the techniques described herein are automated and not myopic—when these techniques are used to determine whether a variant is present at a particular position the sequence data, that determination is made based, at least in part, on one or more variants identified at one or more other positions in the sequence data. The inventors have recognized the presence of a particular type of variant at a particular position (e.g., position n) may provide information about the type of variant (if any) likely present at another position (e.g., position n−2, n−1, n+1, n+2, etc.). Unlike conventional myopic techniques, the techniques developed by the inventors for combining results obtained by multiple different variant callers can take advantage of such information, which leads to improved overall performance.

Some embodiments described herein address all of the above-described issues that the inventors have recognized with conventional variant identification techniques. However, not every embodiment described herein addresses every one of these issues, and some embodiments may not address any of them. As such, it should be appreciated that embodiments of the technology described herein are not limited to addressing all or any of the above-discussed issues of conventional variant identification techniques.

Accordingly, some embodiments involve accessing information specifying multiple sets of variants in sequence data relative to reference sequence data (i.e., variant calls), with each of the multiple sets of variants being generated by using a respective variant identification technique, and determining, using the accessed information, a reconciled set of variants in the sequence data relative to the reference sequence data. Determining the reconciled set of variants in the sequence data may include determining whether a variant is present at a particular position in the sequence data based, not only on variants identified by the variant identification techniques at the particular position, but also on one or more variants identified by the variant identification techniques at one or more other (e.g., all) positions in the sequence data. In this way, the techniques, developed by the inventors, for combining results of multiple variant callers are not myopic because they use information about variants identified at multiple different positions to determine whether a variant is present at a particular position in the sequence data.

In some embodiments, the sequence data may include one or more sequence reads obtained by sequencing genetic material in a biological sample (e.g., one or more cells obtained from a person, animal, or plant). For example, sequence data may be obtained, at least in part, by applying next generation sequencing technology to a biological sample. Prior to application of variant identification techniques, the sequence data may be aligned to reference sequence data, which, for example, may be a reference genome (e.g., the hg19 or hg39 human reference genomes) or any other reference sequence data relative to which it may be meaningful to identify variants in the sequence data obtained by sequencing the genetic material in the biological sample. The sequence data may be aligned to the reference sequence data in any suitable way, as aspects of the technology described herein are not limited in this respect. After the sequence data is aligned to the reference sequence data, multiple variant identification techniques may be applied to the sequence data and the variants identified (or "called") by these variant callers may be reconciled using any of the techniques described herein to obtain a reconciled set of variants in the sequence data relative to the reference sequence data.

In some embodiments, determining the presence of a variant (in the reconciled set of variants) at a particular position is performed by using a statistical model of variant dynamics across positions of a genomic sequence. The statistical model may encode information indicating the likelihood that a particular type of variant is present at one position in the sequence data given that a variant is present at another (e.g., the preceding or the following) position in the sequence data. As such, the statistical model of variant dynamics may be used to obtain (e.g., access, look up, and/or calculate) a likelihood that a first type of variant is present at a first position in the sequence data given that a second type of variant (which may be the same type of variant as the first type or a different type of variant) is present at a second position in the sequence data. The second position may precede (e.g., immediately precede) or follow (e.g., immediately follow) the first position. Accordingly, use of a statistical model of variant dynamics allows the determination of whether a variant is present at a particular position in the sequence data to be based on one or more variants identified at one or more other positions in the sequence data, which is something that is not possible when using myopic techniques for combining output of multiple variant callers. In some embodiments, the statistical model of variant dynamics may be estimated from simulated and/or actual sequence data.

In some embodiments, performance characteristics of one or more of the variant identification techniques whose results are being combined may be used to influence the way in which the results are combined. In this way, when a variant identification technique performs poorly with regard to a particular type of variant (e.g., the technique often misses identifying insertions or deletions that are present, the technique often incorrectly determines that an insertion or a deletion is present, etc.), results produced by the variant identification technique with regard to the particular type of variant may influence the reconciled set of variants less (e.g., by being given less weight) than results produced by other variant identification techniques that perform better with regard to the particular type of variant. For example, in some embodiments, the false negative rate, the true negative rate, the false positive rate, the true positive rate, the precision, the accuracy, the specificity, and/or the sensitivity of one or more variant identification techniques may be used to influence the way in which results produced by the one or more variant identification techniques are used to obtain a reconciled set of variants.

In some embodiments, for example, a first set of variants obtained by using a first variant identification technique and a second set of variants obtained by using a second variant identification technique may be combined to generate a reconciled set of variants based, at least in part, on a measure of a true positive rate and/or a false negative rate of the first variant identification technique for a particular type of variant. In some instances, the combination may be made based on a measure of a true positive rate and/or a false negative rate of each of the first and second variant identification techniques for each type of variant. The measure of a true positive rate and/or a false negative rate (or any other suitable performance characteristic) of a variant identification technique may be estimated using simulated and/or actual sequence data.

In some embodiments, determining the reconciled set of variants in the sequence data from multiple sets of variants may be performed using any suitable technique that is able to take as input the multiple sets of variants, a statistical model of variant dynamics, and/or performance characteristics of one or more of the variant identification techniques used to obtain the multiple sets of variants being combined. For example, in some embodiments, a forward backward algorithm for hidden Markov models (HMMs) may be used to determine the reconciled set of variants. Additionally or alternatively, belief propagation, a Viterbi algorithm, or any other suitable Bayesian updating algorithm may be used to determine the reconciled set of variants.

In some embodiments, determining the reconciled set of variants from multiple sets of variants may be performed using an alignment-based approach in which each variant in the multiple sets is assigned a penalty and the reconciled set of variants is obtained by minimizing the overall penalty of variants selected from the multiple sets of variants. For example, in some embodiments, determining the reconciled set of variants in the sequence data comprises generating a graph of variant calls from the multiple sets of variants being reconciled, assigning costs to nodes in the graph of variant calls based on the penalties associated with the types of variants the nodes represent, and identifying a minimum cost path through the graph of variant calls. In turn, the minimum cost path in the graph indicates the variants that should be in the reconciled set of variants. Because the minimum cost path is identified by minimizing costs across the entire graph, the variants in the reconciled set of variants are identified jointly, rather than independently of one another, as is done by conventional myopic techniques for combining results from multiple variant callers. In this way, the variants identified at one position in the sequence data (e.g., corresponding to a particular point in the path) may influence which variants are identified at another position in the sequence data.

In some embodiments, the minimum cost path may be identified using a Smith-Waterman alignment technique subject to one or more constraints. One example of such a constraint is that any variant in the reconciled set of variants must be selected from the multiple sets of variants being reconciled. Enforcing such a constraint produces a reconciled set of variants that does not include any new variants and includes only those variants that were already identified by at least one of the variant callers whose results are being combined. Another example of a constraint is that the reconciled set of variants must be feasible relative to the reference sequence data such that the reconciled set of variants does not include a set of mutually inconsistent variants. For example, no more than one variant may be identified in the reconciled set of variants for a particular position in the sequence data. As another example, overlapping variants may be identified so long as their associated nucleotides are consistent with one another. Aspects of this technique are described in more detail below with reference to FIGS. 5A-5D.

It should be appreciated that the techniques described herein may be used to identify any suitable type of variant including, but not limited to, insertions, deletions, inversions, single nucleotide polymorphisms (SNPs or SNVs), and multi-nucleotide polymorphisms, as aspects of the technology described herein are not limited in this respect. As the techniques described herein may be used to combine multiple sets of variants produced by multiple variant callers, any such technique may be referred to as a "variant caller caller," a "variant caller combination" technique or a VCC technique.

It should be appreciated that the various aspects and embodiments described herein be used individually, all together, or in any combination of two or more, as the technology described herein is not limited in this respect.

FIG. 1 is a diagram of an illustrative data processing pipeline 100 for identifying a set of variants in sequence data relative to reference sequence data by using multiple variant identification techniques, in accordance with some embodiments of the technology described herein. As shown in FIG. 1, multiple variant identification techniques 104-1, 104-2, . . . , 104-$n$ may be applied to sequence data 102, which has been aligned to reference sequence data 103, to produce respective sets of identified variants (i.e., variant calls) 106-1, 106-2, . . . , 106-$n$. For example, the set of variants 106-1 may be obtained by applying variant identification technique 104-1 to sequence data 102 in view of its alignment to reference sequence data 103. Similarly, the set of variants 106-2 may be obtained by applying variant identification technique 104-2 to sequence data 102 in view of its alignment to reference sequence data 103, and the set of variants 106-$n$ may be obtained by applying variant identification technique 104-$n$ to sequence data 102 in view of its alignment to reference sequence data 103.

In turn, a variant caller combination (VCC) technique 108 may be used to determine a reconciled set of variants 112 based, at least in part, on the sets of identified variants 106-1, 106-2, . . . , 106-$n$. In some embodiments, the VCC technique 108 may determine the reconciled set of variants 112 further based on auxiliary information 110. The auxiliary information may be any suitable type of information that may facilitate determining a reconciled set of variants from multiple sets of variants. For example, the auxiliary information 110 may include a statistical model of variant dynamics. As another example, the auxiliary information 110 may include information about the performance characteristics (e.g., the false negative rate, the false positive rate, the true negative rate, the true positive rate, the precision, the accuracy, the specificity, the sensitivity, etc.) of one or more of the variant identification techniques 104-1, 104-2, . . . , 104-$n$ as a whole and/or with respect to one or more types of variants. As yet another example, in embodiments where the variant caller combination technique 108 identifies a low (e.g., minimum) cost path through a graph generated from the identified variants 106-1, 106-2, . . . , 106-$n$, the auxiliary information may include information indicating penalties associated with one or more types of variants, which in turn may be used to assign costs to nodes in the graph.

It should be appreciated that variant caller combination (VCC) technique 108 may be any suitable VCC technique described herein and, for example, may be any of the VCC techniques described with reference to FIG. 4 and FIGS. 5A-5D.

In some embodiments, the VCC technique 108 does not introduce any new variants that were not already identified by at least one of the variant identification techniques 104-1, 104-2, . . . , 104-$n$. In this way, each of the variants in the reconciled set of variants 112 is present in at least one or more of the sets of identified variants 106-1, 106-2, . . . , 106-$n$.

The data processing pipeline 100 may be executed using one or multiple processors, as aspects of the technology described herein are not limited in this respect. In some embodiments, for example, each of variant identification techniques 104-1, 104-2, . . . , 104-$n$ and VCC technique 108 may be executed using one processor and/or one computer. In other embodiments, the variant identification techniques 104-1, 104-2, . . . , 104-$n$ may be executed on one or more processors and/or computers different from the one or more processors and/or computers used to execute VCC technique 108.

The variant caller combination technique 108 may be used to combine results generated by any suitable number of variant identification techniques. For example, the VCC technique 108 may be used to combine 2, 3, 4, 5, 6, 7, 8, 9, 10, at least two, at least three, at least four, at least five, or at least ten sets of variants produced by respective variant identification techniques. As another example, the VCC technique may be used to combine any number of sets of variants in the range of 2-10 sets of variants, 2-20 sets of variants, 5-50 sets of variants, 10-100 sets of variants, or any other suitable range within a union of the preceding ranges.

Figure 2:
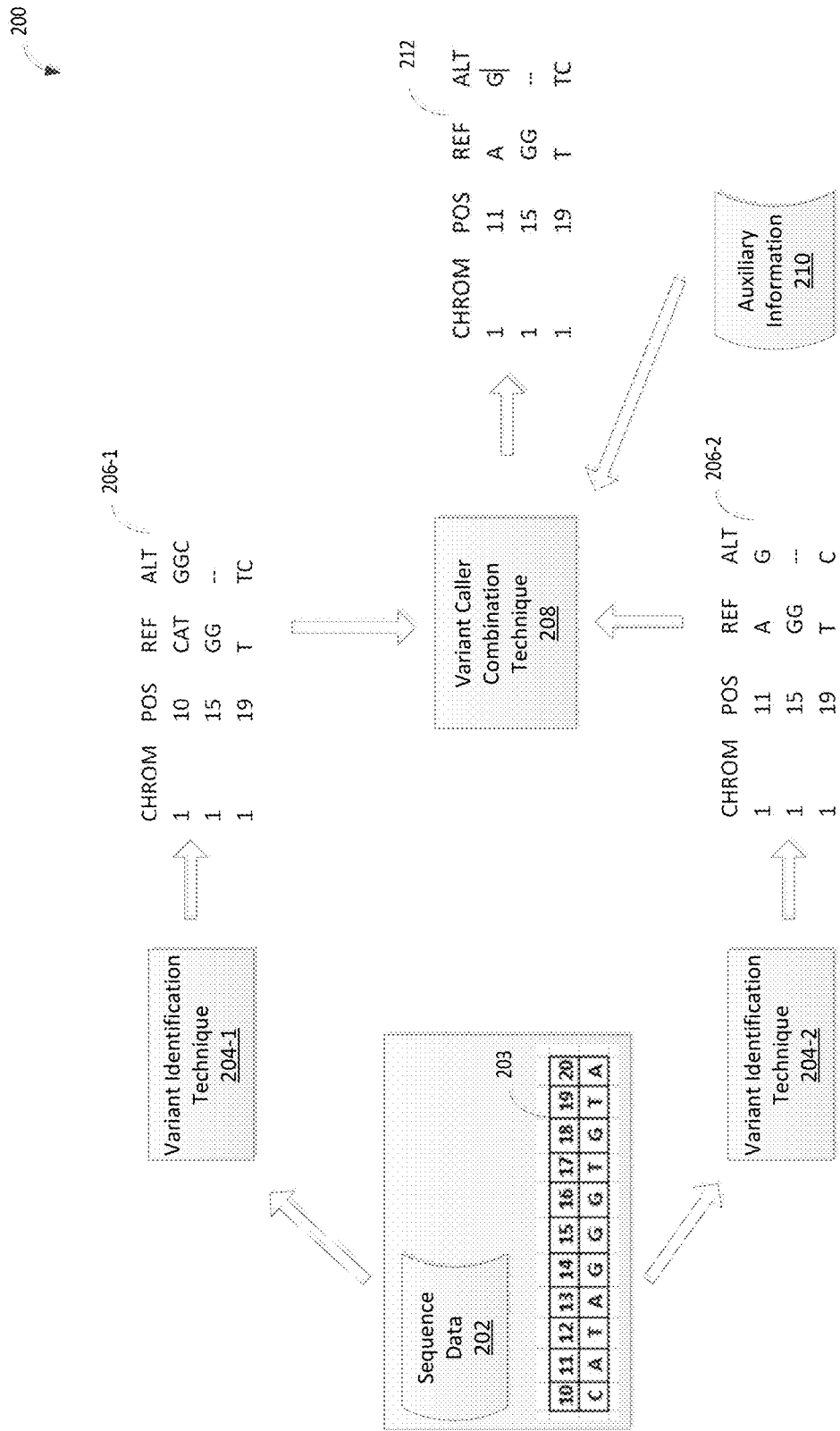
FIG. 2 is another diagram of an illustrative data processing pipeline for identifying a set of variants in sequence data relative to reference sequence data by using multiple variant identification techniques, in accordance with some embodiments of the technology described herein. This figure includes SEQ ID NO: 1.

FIG. 2 is another diagram of an illustrative data processing pipeline 200 for identifying a set of variants in sequence data relative to reference sequence data by using multiple variant identification techniques, in accordance with some embodiments of the technology described herein. As shown in FIG. 2, in the pipeline 200, variant identification technique 204-1 is applied to sequence data 202, which has been aligned to reference sequence data 203, to obtain the set of variants 206-1. Variant identification technique 204-2 is also applied to sequence data 202 to obtain the set of variants 206-2. In turn, variant caller combination technique 208, which may be any suitable VCC technique described herein, combines variant sets 206-1 and 206-2, using auxiliary information 210, to obtain reconciled set of variants 212. The auxiliary information 210 may be any suitable information that may facilitate determining a reconciled set of variants from multiple sets of variants and, for example, may include any of the types of auxiliary information described above with respect to data processing pipeline 100 shown in FIG. 1.

As shown in the illustrative embodiment of FIG. 2, reference sequence data 203 includes the nucleotide sequence "CATAGGGTGTA" (SEQ ID NO: 1) starting at position 10. As can be seen from variant set 206-1, variant identification technique 204-1 has determined that the sequence data 202 has variants at positions 10, 15, and 19 relative to the reference sequence data 203. Specifically, variant identification technique 204-1 identified that: (1) sequence data 202 includes the sequence GGC starting at position 10, whereas the reference sequence data 203 includes the sequence "CAT" starting at position 10, which is a polymorphism of length 3; (2) sequence data 202 contains a deletion at position 15 relative to the reference sequence data 203 which contains the sub-sequence "GG" at position 15; and (3) sequence data 202 contains the sub-sequence "TC" at position 19 (reflecting an insertion of "C" after the "T"), whereas reference sequence data 203 contains only the sequence "T" starting at position 19. On the other hand, as can be seen from variant set 206-2, variant identification technique 204-2 has determined that the sequence data has variants at positions 11, 15, and 19. Specifically, variant identification technique 204-2 identified that: (1) there is an SNP at position 11 because the sequence data 202 has a "G" at position 11, whereas the reference sequence has an "A" at the same position; (2) sequence data 202 contains a deletion at position 15 relative to the reference which contains the sub-sequence "GG" at position 15; and (3) there is an SNP at position 19 because the sequence data 202 has a "C" at position 19, whereas the reference sequence 203 has a "T" at the same position.

As can be seen from example variant caller results shown in FIG. 2, variant identification techniques 204-1 and 204-2 produce results that agree in some parts (e.g., with respect to the presence of an "G" at position 11 and a deletion at position 15) and are inconsistent in other parts (e.g., with respect to calls made at positions 10, 12, and 19), which again illustrates the need for the variant caller combination techniques described herein. Application of the VCC technique 208 to the variant sets 206-1 and 206-2 generates the reconciled set 212.

Figure 3:
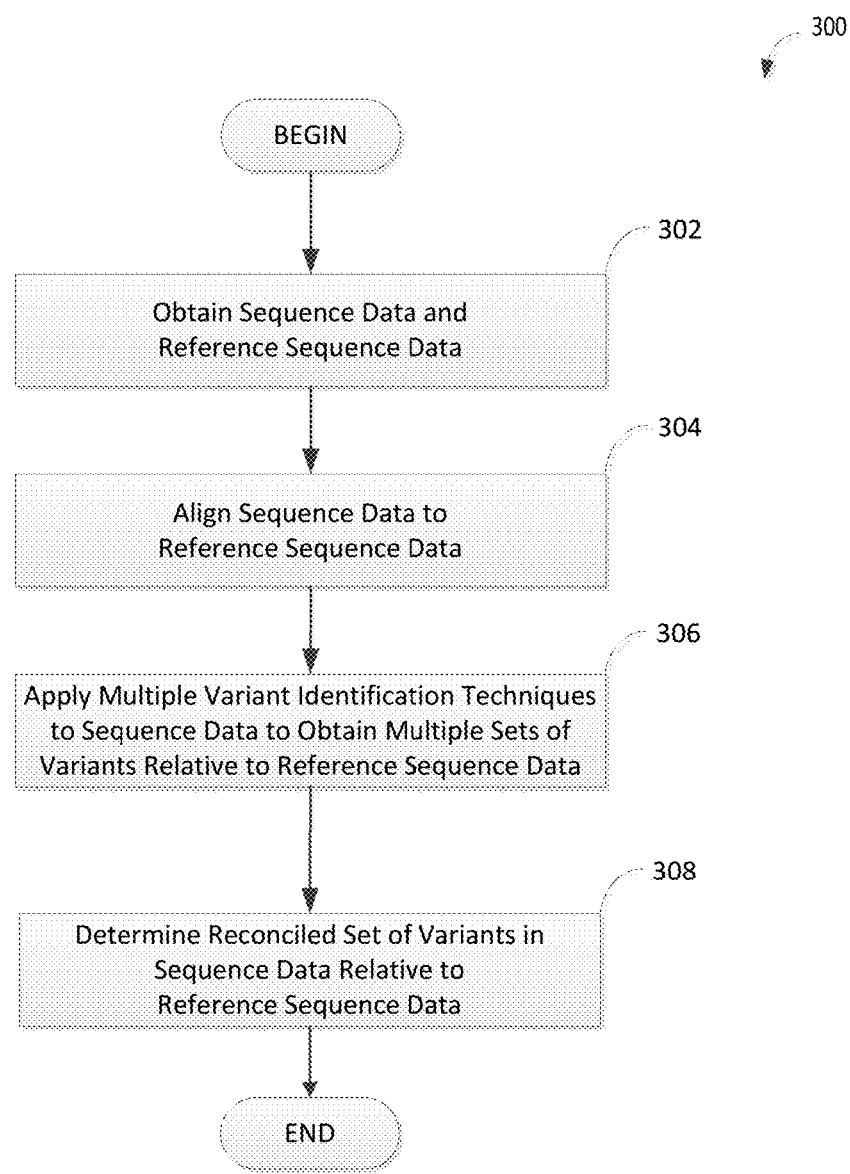
FIG. 3 is a flow chart of an illustrative process for identifying a set of variants in sequence data relative to reference sequence data by combining results obtained using multiple variant identification techniques, in accordance with some embodiments of the technology described herein.

FIG. 3 is a flow chart of an illustrative process 300 for identifying a set of variants in sequence data relative to reference sequence data by combining results generated by multiple variant identification techniques, in accordance with some embodiments of the technology described herein. Process 300 may be performed by any suitable computing device or devices, as aspects of the technology described herein are not limited by the number of computing devices used to perform process 300.

Process 300 begins at act 302, where sequence data and reference sequence data are obtained. The sequence data and reference sequence data may be obtained from any suitable source and may be in any suitable format, as aspects of the technology described herein are not limited in this respect. The sequence data may be obtained by sequencing one or more biological samples (e.g., using next generation sequencing and/or any other suitable sequencing technique or technology) and may include sequence reads obtained as a result of the sequencing. The reference sequence data may be a reference genome (e.g., the hg19 or hg39 human reference genomes) or any other reference sequence data relative to which it may be meaningful to identify variants in the obtained sequence data.

Next, process 300 proceeds to act 304, where the sequence data is aligned to the reference sequence data. The alignment may be performed using any suitable alignment tool(s) and/or technique(s), as aspects of the technology described herein are not limited in this respect. Non-limiting examples of software tools that may be used to perform alignment in some embodiments include the Bowtie2 alignment tool, the Burrows-Wheeler Aligner (BWA) alignment tool, the CUSHAW3 alignment too, the MOSAIK alignment tool, and the Novoalign alignment tool. Another technique that may be used to perform alignment, in some embodiments, is a technique for aligning sequence reads to a graph described in U.S. Pat. Pub. No. 2015/0057946, titled "METHODS AND SYSTEMS FOR ALIGNING SEQUENCES," which is incorporated by reference herein in its entirety.

Next, process 300 proceeds to act 306, where multiple variant identification techniques are applied to the sequence data to obtain multiple sets of variants relative to the reference sequence data to which the sequence data was aligned at act 304. Any suitable number of variant identification techniques may be applied to the sequence data at act 306. Examples of variant identification techniques that may be applied at act 306 include, but are not limited to, the Genome Analysis Tool Kit HaplotypeCaller (GATK-HC), GATK UnifiedGenotyper, SAMtools mpileup, FreeBayes, Ion Proton Variant Caller, SNPSVM, and Atlas 2. In some embodiments, a variant identification technique may be configurable by setting values for one or more parameters.

Another example of a variant-identification technique, which may be used in some embodiments, is a graph-based technique described in U.S. Pat. No. 9,116,866, titled "Methods and Systems for Detecting Sequence Variants," which is incorporated by reference herein in its entirety. Accordingly, applying multiple variant identification techniques, at act 306, may include applying a configurable variant identification technique to the sequence data multiple times, but with one or more of the parameter values being changed between applications.

In some embodiments, a set of variants generated by a variant identification technique may include information identifying one or more variants occurring in the sequence data relative to the reference sequence data. For a particular variant, such information may identify the type of variant (e.g., an SNP, an insertion, a deletion, etc.), the position of the variant relative to the reference sequence, an indication of the allele where the variant occurs, the length of the variant (e.g., the length of a polymorphism when the variant is a polymorphism, the length of an inserted sequence when the variant is an insertion, the length of a deleted sequence when the variant is a deletion), one or more nucleotides associated with the variant (e.g., the nucleotide in the mutation when the variant is an SNP, the nucleotide(s) in the inserted sequence when the variant is an insertion), and/or any other suitable information. The set of variants generated by a variant identification technique may be in a file conforming to the variant call format (a VCF file) or in any other suitable format, as aspects of the technology described herein are not limited in this respect.

Next, process 300 proceeds to act 308, where a variant caller combination technique is applied to the multiple sets of variants identified at act 306 to generate a reconciled set of variants in the sequence data relative to the reference sequence data. This may be done using any of the techniques described herein, including, for example, the techniques described with reference to FIGS. 4 and 5.

In some embodiments, the variant caller combination technique used at act 308 may determine whether a first variant is present at a first position in the sequence data based, at least in part, on one or more variants at one or more other positions in the sequence data. For example, the VCC technique used at act 308 may make such a determination by using a statistical model of variant dynamics, which encodes information indicating the likelihood that a particular type of variant is present at one position in the sequence data given that a variant is present at another (e.g., the preceding or the following) position in the sequence data. Using the statistical model of variant dynamics in furtherance of determining whether a variant is present at a particular position allows that determination to be influenced by the variants identified as being present at one or more preceding and/or subsequent positions in the sequence data.

As another example, the VCC technique used at act 308 may involve generating a graph of variant calls from the multiple sets of variants being reconciled, assigning costs to nodes in the graph of variant calls, and identifying a low (e.g., minimum) cost path through the graph of variant calls to identify the variants in the reconciled set of variants. Because the low cost path is identified by minimizing costs across the entire graph, the variants in the reconciled set of variants are identified jointly, rather than independently of one another, so that the variants identified at one position in the sequence data may influence which variants are identified at another position in the sequence data.

Figure 4:
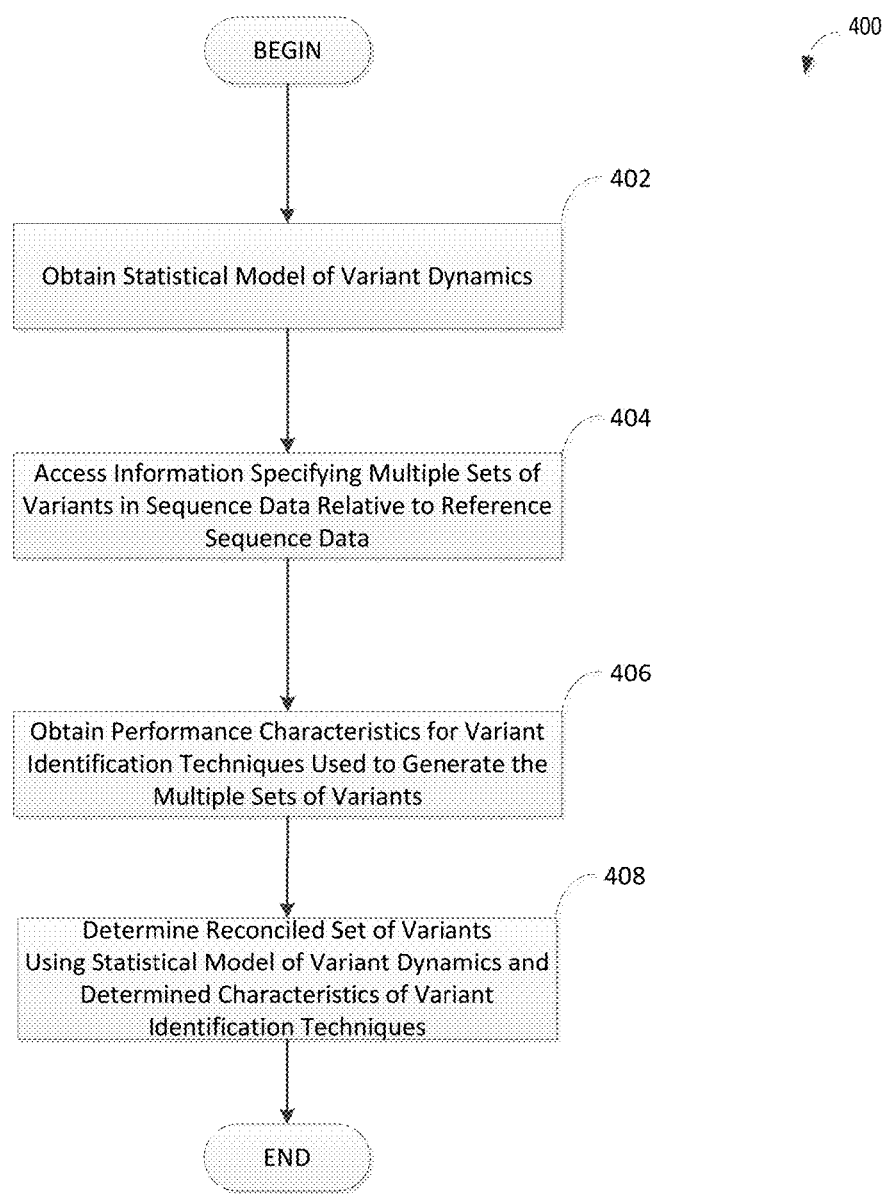
FIG. 4 is a flow chart of an illustrative process for generating, from multiple sets of variants identified by respective variant identification techniques, a reconciled set of variants specifying variants in sequence data relative to reference sequence data, in accordance with some embodiments of the technology described herein.

FIG. 4 is a flow chart of an illustrative process 400 for generating, from multiple sets of variants identified by respective variant identification techniques, a single reconciled set of variant calls specifying variants in sequence data relative to reference sequence data, in accordance with some embodiments of the technology described herein. The process 400 may be performed by any suitable number of computing devices of any suitable type, as aspects of the technology described herein are not limited in this respect.

Process 400 begins at act 402, where a statistical model of variant dynamics is obtained. The statistical model of variant dynamics may encode information indicating a likelihood or probability that a particular type of variant is present at one position in the sequence data given that one or more variants are present at one or more other (preceding and/or following) positions in the sequence data. For example, the statistical model of variant dynamics may encode information indicating a likelihood or probability that a variant of type "T1" is present at a particular position (e.g., position n) given that another variant (e.g., a variant of type "T1" or of another type) is present at a preceding position (e.g., position n−1, n−2, n−3, etc.). As another example, the statistical model of variant dynamics may encode information indicating a likelihood or probability that a variant of type "T1" is present at a particular position given that multiple variants of respective types are present at positions preceding the particular position. As yet another example, the statistical model of variant dynamics may encode information indicating a likelihood or probability that a variant of type "T1" is present at a particular position given that one or multiple variants of respective types are present at one or multiple positions following the particular position.

In some embodiments, the statistical model of variant dynamics may encode information indicating a likelihood or probability that a variant having one set of characteristics is present at one position in the sequence data given that one or more variants having respective set(s) of characteristics are present at one or more other (preceding and/or following) positions in the sequence. The level of resolution at which the statistical model jointly models the variants may depend on the amount of information in the set of characteristics. Generally, the more information in the set of characteristics, the finer the resolution of the statistical model. One may think of the set of characteristics associated with a variant at a particular position as a "state" of the genomic object this position.

For example, the set of characteristics for a variant may include the type of the variant. In such implementations, the statistical model may encode information indicating that a particular type of variant is present at a particular position given that one or more other variants of respective types are present at one or more other positions in the sequence data. As another example, the set of characteristics for a variant may include the type of variant and a length associated with the variant (e.g., the length of an insertion or deletion). In such implementations, the statistical model may encode information indicating that a particular type of variant having a certain length (or of any suitable length) is present at a particular position given that one or more variants of respective types and lengths are present at one or more other positions in the sequence data. As yet another example, the set of characteristics for a variant may include the type of variant and nucleotide information associated with the variant. In such implementations, the statistical model may encode information indicating that a particular type of variant associated with a particular nucleotide sequence is present at a particular position given that one or more variants of respective types and being associated with respective nucleotide sequences are present at one or more other positions in the sequence data. Still other implementations are possible.

As the foregoing examples illustrate, a statistical model of variant dynamics may model the dependencies among variants at different levels of resolution. As one example, a statistical model of variant dynamics may model the likelihood or probability that a particular type of variant appears at a particular position based only on the types of other variants appearing at one or more other positions. As another example, a statistical model of variant dynamics at a finer level of resolution may model the likelihood or probability that a variant (of a particular type and, optionally, length) appears at a particular position based on the types and lengths of other variants appearing at one or more other positions. As yet another example, a statistical model of variant dynamics at an even finer level of resolution may model the likelihood or probability that a variant (of a particular type and, optionally, length and associated nucleotide(s)) appears at a particular position based on the types of, lengths of, and associated nucleotide(s) associated with one or more other variants appearing at one or more other positions. It should be appreciated, however, that the greater the resolution of a statistical model of variant dynamics, the greater the amount of data required to estimate such a statistical model reliably.

In some embodiments, a statistical model of variant dynamics may be encoded in at least one data structure comprising any of the above-described information and/or any other suitable information. For example, a statistical model of variant dynamics may be encoded in a data structure storing a table or matrix with rows and columns corresponding to different types of variants, such that the value stored at row j and column k of the table or matrix represents the likelihood or probability that a variant of type "k" follows a variant of type "j." It should be appreciated, however, that a statistical model of variant dynamics is not limited to being encoded in any particular type of data structure(s), as aspects of the technology described herein are not limited in this respect.

By way of introducing notation to represent some types of statistical models of variant dynamics, let the set of all possible types of variants be $\{v \in V\}$, and let there be N positions $\{1 \leq n \leq N\}$ in the reference sequence data. Let the set V also include the element $\phi$ representing "no variant." Let $r_n^v$ represent the event that the true variant at position n is the variant of type $v \in V$. Then, one illustrative type of statistical model of variant dynamics, may be represented by the notation $P(r_n^v | r_{n-1}^u)$. As suggested by this notation, this illustrative type of statistical model of variant dynamics may be used to determine the probability that a variant of type 'v' is present at position n given that there is a variant of type 'u' (u and v may the same or different types of variants) present at position n−1. Because the set V includes the element $\phi$, representing "no variant," this illustrative statistical model of variant dynamics may be also used to determine the probability that a variant of a particular type is present at position n given that no variant is present at position n−1 and, conversely, a probability no variant is present at position n given that a variant of a particular type is present at position n−1.

In some embodiments, for much of a given reference genome, the probability of two variations of the same type (such as SNPs) occurring at adjacent loci may be relatively small. For example, $P(r_n^{SNP}|r_{n-1}^{SNP}) \ll P(r_n^{SNP}|r_{n-1}^{\phi}) \ll P(r_n^{\phi}|r_{n-1}^{\phi})$. The second inequality follows from the fact that, out of 3 billion bases in the human genome, less than 100 million have been found to be different from the reference.

It should be appreciated, however, that there are many types of statistical models of variant dynamics. For example, another type of statistical model of variant dynamics may be represented by the notation $P(r_n^v | r_{n-1}^u, r_{n-2}^w)$. This type of model may be used to determine the probability that a variant of type 'v' is present at position n given that a variant of type 'u' (or no variant) is present at position n−1 and a variant of type w (or no variant) is present at position n−2. More generally, a causal statistical model of variant dynamics may be used to determine the probability that a variant of type 'v' is present at position n given one or more variants present at one or more positions preceding position n. A non-causal statistical model of variant dynamics may be used to determine the probability that a variant of type 'v' is present at position n given one or more variants present at one or more different positions (e.g., one or more positions preceding n and/or one or more positions following n).

In some embodiments, obtaining the statistical model of variant dynamics at act 402 may include accessing an existing statistical model of variant dynamics. The existing statistical model may have been previously estimated from data. In other embodiments, obtaining the statistical model of variant dynamics at act 402 may include estimating it from data as part of process 400.

A statistical model of variant dynamics may be estimated from data in any suitable way. In some embodiments, for example, a statistical model of variant dynamics may be estimated based on variants previously identified (and, preferably, verified, for example, by hand) in real sequence data relative to reference sequence data. Such an estimate may be obtained, for example, by counting the number of transitions between different types of variants identified in the real sequence data and using the relative frequency of appearance of certain types of variant-to-variant transitions to obtain the probability of transitioning from one type of variant to another. For example, if among the variants identified for real sequence data, the variant of type "T2" follows variant of type "T1" more often than variant of type "T3", the estimated statistical model may include information indicating that the variant of type "T2" is more likely to occur after variant of type "T1" than is the variant of type "T3." The estimated statistical model may further include information indicating the likelihood or probability of a variant of type "T2" following a variant of type "T1" and the likelihood or probability of a variant of type "T3" following a variant of type "T1," with these likelihoods or probabilities being estimated based on the frequency of occurrence, in real sequence data, of transitions from variant of type "T1" to variant of type "T2" and of variant of type "T1" to variant of type "T3."

After the statistical model of variant dynamics is obtained at act 402, process 400 proceeds to act 404, where information specifying multiple sets of variants (i.e., sets of variant calls) in sequence data relative to reference sequence data is accessed. As described herein, each of the multiple sets of variants may be obtained using a respective variant identification technique. The information specifying multiple sets of variants may be obtained from any suitable source and in any suitable format, as aspects of the technology described herein are not limited in this respect. Any suitable number of sets of variants may be obtained at act 404, as aspects of the technology described herein are not limited in this respect.

Next, process 400 proceeds to act 406, where performance characteristics are obtained for each of one or more of the variant identification techniques used to generate the multiple sets of variants. The performance characteristics of a variant identification technique may include, but are not limited to, the false positive rate, true negative rate, false positive rate, true positive rate, precision, accuracy, specificity, false discovery rate, and/or the sensitivity of the variant identification technique overall across all variant types and/or for each one or more types of variants.

In some embodiments, a true positive may correspond to the event that a variant caller correctly determines that a variant is present (e.g., a correct variant allele or position call). A false positive may correspond to the event that a variant caller incorrectly identifies the presence of a variant when none is there (e.g., an incorrect variant allele or position call). A false negative may correspond to the event that a variant caller fails to identify the presence of a variant, where a variant is actually present (e.g., no call). Filtering out ambiguously mapped reads can mitigate FP variant calls due to mapping errors, but may also remove correctly mapped reads with true variants, potentially resulting in false negatives (e.g., incorrect reference genotype). A true negative may correspond to the event that a variant caller correctly determines that no variant is present.

In some embodiments, the frequencies of true positives, true negatives, false positives, and false negatives occurring in the results produced by a variant caller may be used to determine some types of performance characteristics of the variant caller. For example, the false positive rate of a variant caller may be obtained as a ratio of the total number of false positives called relative to the sum of the total number of true negatives and false positives called. As another example, the true positive rate of a variant caller (sometimes termed "sensitivity" or "recall") may be obtained as a ratio of the total number of true positives called relative to the sum of the total number of true positives and false negatives called. As yet another example, the false negative rate of a variant caller may be obtained as a ratio of the total number of false negatives called relative to the sum of the total number of true positives and false negatives called. As yet another example, the true negative rate of a variant caller (sometimes termed "specificity") may be obtained as a ratio of the total number of true negatives called relative to the sum of the total number of true negatives and false positives called. As yet another example, the precision of a variant caller may be obtained as ratio of the number of true positive calls relative to the sum of the total number of true positive calls and false positive calls. As yet another example, the accuracy of a variant caller may be obtained as a ratio of the sum of the true positive and true negative calls relative to the sum of the total number of true positive calls, true negative calls, false positive calls, and false negative calls.

It should be appreciated that the above-described performance characteristics may be used to quantify the performance of a variant caller overall and/or the performance of the variant caller for each of one or more particular types of variants. Thus, for example, one may obtain a false positive rate (and/or any of the other types of performance characteristics described above) for the variant caller with respect to a particular type or types of variants or with respect to all types of variants.

In some embodiments, the performance characteristics of one or more of the variant identification techniques used to generate the multiple sets of variants may be obtained by accessing estimated performance characteristics. The estimated performance characteristics may have been previously obtained from data. In other embodiments, obtaining the performance characteristics at act 406 may include estimating the performance characteristics from (simulated and/or actual) data as part of process 400.

In some embodiments, the performance characteristics of one or more of the variant identification techniques may be estimated using simulated data. For example, simulated data may be obtained by starting from a reference genome, adding one or more controlled mutations to create one or more variant genomes, and generating reads from the variant genome(s). A variant identification technique may then be applied to the generated reads. The obtained results may then be analyzed to determine any of the above-describes quantities such as the number (overall or for particular type(s) of variants) of false positives, false negatives, true positives, true negatives, and/or any of the quantities that may be derived therefrom (e.g., false positive rate, false negative rate, true positive rate, true negative rate, etc.). In some embodiments, the performance characteristics may be obtained by using any suitable bioinformatics software for benchmarking variant identification techniques such as, for example, the Mitty software tool (available at http://latticelabs.github.io/Mitty). It should be appreciated that, in some embodiments, the performance characteristics of a variant identification technique may be estimated using real data (which, for example, has been manually verified) in addition to or instead of using simulated data.

By way of introducing notation to represent some types of performance characteristics of variant callers, let $J=\{j; 1 \leq j \leq J\}$ be the set of variant callers used to generate the multiple sets of variants obtained at act 406. For each $n \in \{1 \ldots N\}$ and each type of variant $v \in V$, let the quantity $\delta_j^{nv} \in \{0,1\}$ take on the value 1 when the j'th variant caller identifies the presence of variation v at position n and take on the value 0 otherwise. Let $\delta^{nv} \in \{0,1\}^J$ represent a J-dimensional binary vector with coordinate j being $\delta_j^{nv}$. Then the quantity $P(\delta_j^v|v)/P(\delta_j^v)$ may represent the true positive rate or the false negative rate of the j'th variant caller for variation v.

After the performance characteristics of one or more of the variant identification techniques are obtained at act 406, process 400 proceeds to act 408, where a reconciled set of variants is determined using the statistical model of variant dynamics obtained at act 402, the multiple sets of variants obtained at act 404, and the performance characteristics obtained at act 406. Accordingly, in some embodiments, act 408 comprises determining whether there is a variant present at a particular position relative to the reference sequence data based on: (1) the variants identified, in the multiple sets of variants obtained at act 404, at the particular position; (2) variants identified, in the multiple sets of variants obtained at act 404, at one or more other positions; (3) the statistical model of variant dynamics obtained at act 402; and (4) the performance characteristics obtained at act 406.

In some embodiments, determining whether there is a variant present at a particular position may further include determining the nature of the variant, for example, by determining the type of variant (e.g., an SNP, an insertion, a deletion, etc.), the length of the variant (e.g., the length of a polymorphism when the variant is a polymorphism, the length of an inserted sequence when the variant is an insertion, the length of a deleted sequence when the variant is a deletion), and/or one or more nucleotides associated with the variant (e.g., the nucleotide in the mutation when the variant is an SNP, the nucleotide(s) in the inserted sequence when the variant is an insertion). Such information may be obtained at act 404 in the multiple sets of variants.

In some embodiments, determining a reconciled set of variants comprises identifying, based on the statistical model of variant dynamics, the multiple sets of variants, and the performance characteristics, the likely (e.g., the most likely) variants in the sequence data relative to the reference sequence data. This may be done in any suitable way. For example, in some embodiments, the likely variants in the sequence data may be determined iteratively starting from the first (or other suitable initial) position, whereby the most likely variant determined to occur at position n−1 may be used to aid in determining the most likely variant (if any) at position n. The amount of influence that the presence of variant at position n−1 has on the determination of presence of another variant at position n may be encoded in the statistical model of variant dynamics.

For example, in some embodiments, determining the most likely sequence of variants may include: (1) determining the likelihoods of variants appearing in the first position based on the performance characteristics of the variant callers obtained at act 406; (2) determining for each position $n>1$ and for each variant $v \in V$, the probability $P(r_n^v|r_{n-1}^u, \delta^{nv})$, which is the probability that the true variation at position n is v, given that the true variation at position n−1 is u and further given the calls $\delta^{nv}$ made by the variant callers (as specified in the multiple variants sets obtained at act 404) at position n for variant v; and (3) selecting, as the reconciled set of variants, the sequence of variants that maximizes the product, across all positions n, of the values $P(r_n^v|r_{n-1}^u, \delta^{nv})$ or, equivalently, maximizes the sum of the corresponding log probabilities.

In some embodiments, the probabilities $P(r_n^v|r_{n-1}^u, \delta^{nv})$ may be calculated iteratively according to:

$$P(r_n^v|r_{n-1}^u, \delta^{nv}) \approx P(r_n^v|r_{n-1}^u)\Pi_j P(\delta_j^v|v)/P(\delta_j^v),$$

where the term $P(r_n^v|r_{n-1}^u)$ represents a statistical model of variant dynamics (obtained at act 402) that provides a probability that there is a variant v at position n given that there is a variant u at position n−1, and where the term $P(\delta_j^v|v)/P(\delta_j^v)$ (obtained at act 406), inside the product, represents either the true positive or the false negative rate of variant caller j for variant v. In this way, the determination of the most likely set of variants is accomplished by using the statistical model of variant dynamics obtained at act 402 and the performance characteristics obtained at act 406. The computations may be guided using a grid of variants specified in the multiple sets of variants obtained at act 404, since only these variants may be part of the set of reconciled variants.

In some embodiments, the above-described computations may be computed by using the Viterbi algorithm, using the forward-backward algorithm for hidden Markov models, or any other suitable Bayesian computation technique. Accordingly, in some embodiments, the reconciled set of variants may be determined by using such techniques to identify a most likely set of variants given the statistical model of statistical variation, the multiple sets of variants produced by respective variant identification techniques, and the performance characteristics of these variant identification techniques.

In some embodiments, the reconciled set of variants may be determined by using a forward-backward algorithm for hidden Markov models, which algorithm can fuse information from the statistical model of variant dynamics obtained at act 402, the variants identified in the multiple sets obtained at act 404, and the performance characteristics obtained at act 406. After the reconciled set of variants is determined at act 408, process 400 completes.

It should be appreciated that process 400 is illustrative and that there are variations of process 400. For example, in some embodiments, the order of the acts 402, 404, and 406 may be different than the order illustrated in FIG. 4. As another example, although in the illustrated embodiment, the reconciled set of variants is obtained using both a statistical model of variant dynamics and performance characteristics of the variant identification techniques being reconciled, in other embodiments the reconciled set of variants may be obtained by using a statistical model of variant dynamics or performance characteristics of the variant identification techniques being reconciled, but not both.

Figure 5A:
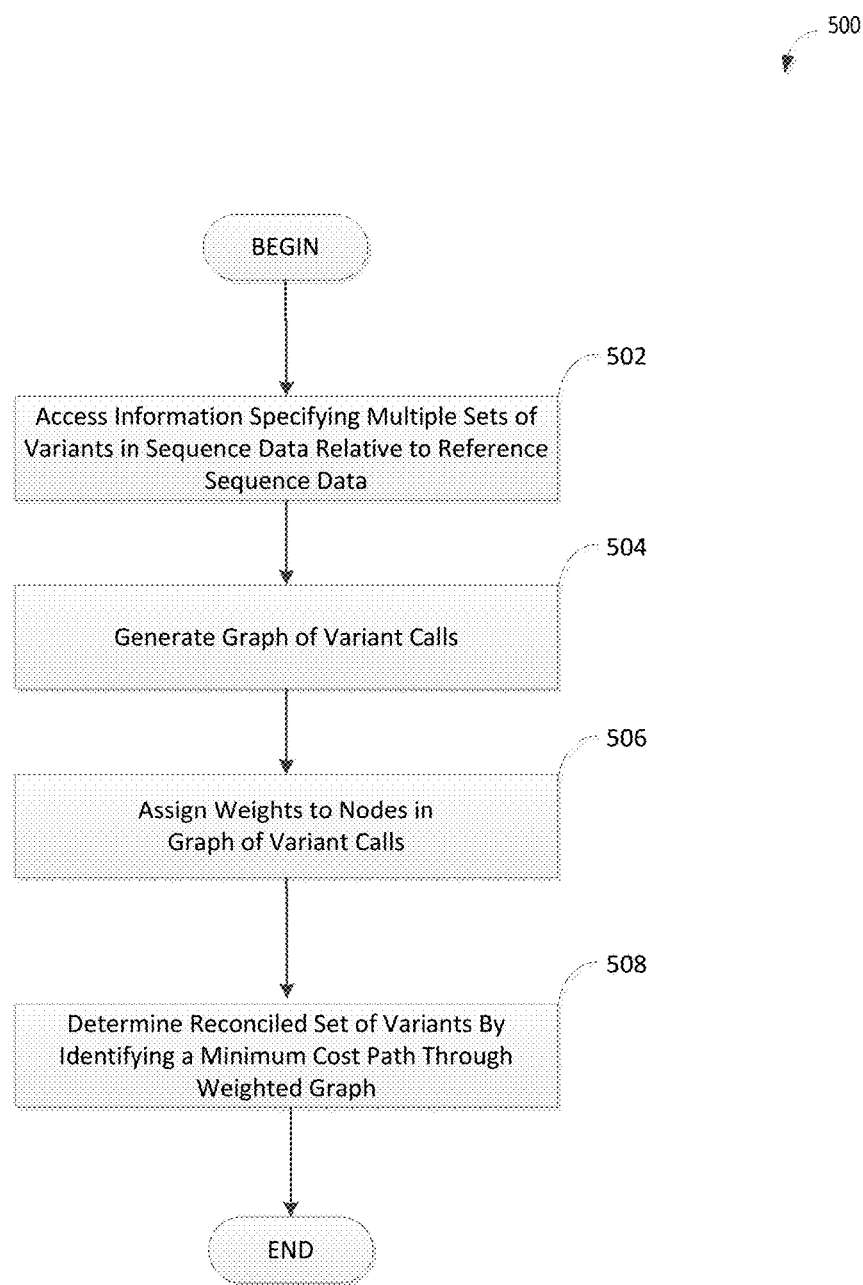
FIG. 5A is a flow chart of another illustrative process for generating, from multiple sets of variants identified by respective variant identification techniques, a reconciled set of variants specifying variants in sequence data relative to reference sequence data, in accordance with some embodiments of the technology described herein.

FIG. 5A is a flow chart of illustrative process 500 for generating, from multiple sets of variants identified by respective variant identification techniques, a single reconciled set of variant calls specifying variants in sequence data relative to reference sequence data, in accordance with some embodiments of the technology described herein. The process 500 may be performed by any suitable number of computing devices of any suitable type, as aspects of the technology described herein are not limited in this respect.

Unlike the process 400 described above, which uses a statistical model of variant dynamics to identify the reconciled set of variants via probabilistic (e.g., Bayesian) techniques, the illustrative process 500 involves identifying the reconciled set of variants using alignment-based techniques, as described in more detail below.

Process 500 begins at act 502, where information specifying multiple sets of variants in sequence data relative to reference sequence data is accessed. Each of the multiple sets of variants may be obtained using a respective variant identification technique. The information specifying multiple sets of variants may be obtained from any suitable source and in any suitable format, as aspects of the technology described herein are not limited in this respect. Any suitable number of sets of variants may be obtained at act 502, as aspects of the technology described herein are not limited in this respect.

Next, process 500 proceeds to act 504, where a graph of variant calls is generated. The generated graph may reflect all the variants in the multiple sets of variants obtained at act 502 relative to the reference sequence data. The graph includes nodes and edges and, in some embodiments, may be a directed acyclic graph. Nodes in the graph may correspond to nucleotides in the reference sequence data or in the variants specified in the multiple sets of variants obtained at act 502.

In some embodiments, the nodes and the edges among them may encode some or all of the nucleotide sequences that may be obtained by modifying the reference sequence based on one or more of the variants in the multiple sets of variants. In such embodiments, an edge in the graph connecting two nodes representing first and second nucleotides may indicate that the first and second nucleotides appear one after the other in at least one nucleotide sequence that may be obtained by modifying the reference sequence based on one or more of the variants in the multiple sets of variants. In this way, the graph of variant calls generated at act 504 may encode (left-to-right) paths relative to the reference sequence. To the extent any left-to-right path deviates from the reference sequence, that deviation reflects a change according to some variant(s) in the multiple sets of variants obtained at act 502.

An illustrative example of a graph of variant calls that may be constructed at act 504 is shown in FIG. 5B. The graph in FIG. 5B was generated by using the reference sequence "CATAGGGTGTA" (SEQ ID NO: 1) (which is part of the reference sequence data 203 described with reference to FIG. 2) and the results 206-1 and 206-2 obtained by applying variant identification techniques 204-1 and 204-2, respectively, to the sequence data 202 in view of the reference sequence data 203. Left-to-right paths in the graph of FIG. 5B indicate nucleotide sequences that may be obtained by modifying the reference sequence based on one or more of the variants in the multiple sets of variants.

For example, the feasible sequences that include the nucleotide "A" in the fourth position, include: (1) the sequence that reaches the "A" in the fourth position on the top line by going along the top (this sequence may be denoted as: C-A-T-A); (2) the sequence that reaches the "A" in the fourth position by starting at the top and going down to the "G" and back up to the "T" before reaching the "A" (this sequence may be denoted as: C\G/T-A); and (3) the sequence that follows the bottom nucleotides "GGC" before going up to the "A" in the fourth position (this sequence may be encoded as: G-G-C/A).

The inventors recognized that, since the graph of variant calls encodes all the variants identified by the multiple variant callers, each left-to-right path through the graph may correspond to a possible way of reconciling the results generated by the variant callers. Thus, a reconciled set of variants may be identified from the graph of variant calls by identifying a single left-to-right path in the graph of variant calls based on one or more criteria. The inventors have further recognized that one way to identify, in the graph, a left-to-right path that represents the reconciled set of variants is to penalize each candidate path based on the extent of its divergence from the reference sequence (different types of variants may be penalized differently or by the same amount), and identifying, from among the penalized candidate paths, a single left-to-right path in the graph that is: (1) everywhere coincident with at least one of the variant callers' paths; and (2) minimizes the path penalty.

Accordingly, in the embodiment illustrated in FIG. 5A, after a graph of variant calls is generated at act 504, process 500 proceeds to act 506, where a cost is assigned to each of one or more nodes in the graph, and subsequently to act 508, where the assigned costs are used to identify a minimum cost path through the graph.

In some embodiments, the cost assigned to a node in the graph of variant calls may be determined based on penalties associated with one or more types of variants. In some instances, the penalties for different types of variants may be different, whereas, in other instances, two different types of variants may incur the same penalty. For example, the penalty for a polymorphism may be different from a penalty for an insertion or a deletion. As another example, the penalty for an insertion may be different from a penalty for a deletion. As yet another example, insertions of different lengths may be penalized differently. As yet another example, deletions of different lengths may be penalized differently.

In some embodiments, the penalties to use as part of process 500 may be obtained prior to the execution of process of process 500 and may be accessed as part of act 504. In other embodiments, the penalties to use part of process 500 may be estimated from data, as part of process 500 (e.g., during act 504). Whether or not estimated as part of process 500, the penalties may be estimated in any suitable way and, for example, may be estimated by counting the frequencies of different types of variations in a corpus of training data comprising variants identified by one or more variant callers on simulated and/or actual data.

After the costs are assigned to each of the nodes at act 506, process 500 proceeds to act 508 where the minimum cost path through the graph is identified. The minimum cost path may be identified using any suitable (e.g., dynamic programming) technique for identifying minimum cost paths in a directed graph, as aspects of the technology described herein are not limited in this respect. In turn, the minimum cost path specifies the reconciled set of variants to output (e.g., as a VCF file or in any other suitable format). After the reconciled set of variants is identified at act 508, process 500 completes.

In some embodiments, a minimum cost path may be identified using a two-part iterative process: (1) a forward pass in which the costs assigned to the nodes are used to compute scores for the nodes, a node's score representing a cumulative cost of a least-cost path through the graph up to and including the node; and (2) a backwards pass during which the computed scores are used to identify the minimum cost path.

In the forward pass, the scores for nodes may be calculated iteratively, left-to-right. A score for a first node (which may be at any position n relative to the reference sequence) may be computed based on penalties associated with different types of variants called (by the variant callers whose results are being combined) at position n and an already-computed score for a second node in the graph located to the left of the first node (at position n−1 relative to the reference sequence). In some embodiments, this score for the first node may be calculated as a maximum of the following four quantities:

(1) the already-computed score for the second node plus a match bonus (a "negative" penalty), if the first and second nodes correspond to consecutive positions in the reference and the nucleotide at the first node matches the corresponding nucleotide in the reference;

(2) the already-computed score for the second node plus a mismatch penalty, if the first and second nodes correspond to consecutive positions in the reference and the nucleotide at the first node does not match the corresponding nucleotide in the reference;

(3) the already-computed score for the second node plus a deletion penalty, if the first and second nodes do not correspond to consecutive positions in the reference and the path between the first and second nodes implies a deletion; and (4) the already-computed score for the second node plus an insertion penalty, if the two nodes do not correspond to consecutive positions in the reference and the path between the nodes implies an insertion.

In some instances, a node in a graph of variant calls may have more than one node to its left, in which case the maximum is taken over the set that includes each of the above-listed four quantities for all those nodes to the left that are consistent with a branch implied by a variant in one of the sets of variants obtained at act 502. That is, a path may not include a path from node A to node B to node C if there is no single variant identified by one of the variant callers that implies a path from node A to node B to node C. In this sense, the technique may be considered a modified Smith-Waterman algorithm in that the maximum is not taken over all nodes in the graph as in the Smith Waterman algorithm.

As one illustrative example of assigning scores to vertices in a graph of variant calls, let the penalties associated with different types of variants be: 2 points for matches, −3 points for insertion and deletion beginnings, −1 point for insertion and deletion extensions, and −2 points for polymorphisms (i.e., mismatches). Applying the above-described score assignment scheme using these penalty values to the graph of variant calls shown in FIG. 5B results in the assigned scores shown in FIG. 5C. A scoring system in which penalties are posited as the logarithm of the empirical frequency of various mutation types (e.g., match, mismatch, insertion, deletion) may be used to obtain the final score that corresponds to the logarithm of the probability of observing all of the variants together. Such a scoring scheme may lead to the discovery of the most likely sequence of variants.

After the forward pass is completed, the calculated scores may be used to identify the minimum cost path through the graph. This may be accomplished using any suitable technique (e.g., dynamic programming). Continuing the example of FIGS. 5B and 5C, FIG. 5D shows a minimum cost path (which scores 3), identified in the graph of variant calls of FIG. 5B, indicating a reconciled set of variant calls, in accordance with some embodiments of the technology described herein. The identified path corresponds to the reconciled set of variants 212 shown in FIG. 2.

As may be appreciated from the foregoing, the process 500 may be considered a global optimization algorithm that identifies a reconciled set of variant calls as a sequence that minimizes the divergence of the sample genomic sequence from the reference sequence. The minimum cost path identified by process 500 will often be very different from a sequence of locally optimal variant calls, as may be determined by a myopic conventional technique for combining variant calls made by multiple variant callers because such techniques do not take into account the overall cost of all of the local calls made. The minimum cost path may be considered to represent the globally most likely sequence of edit operations needed to convert the reference genome into the sampled genome. The constraints ensure that there is prior evidence for each edit operation, and evidence is prioritized by likelihood of occurrence (e.g., if penalties are estimated as frequencies or log-frequencies on a large corpus of variant calls).

Figure 6:
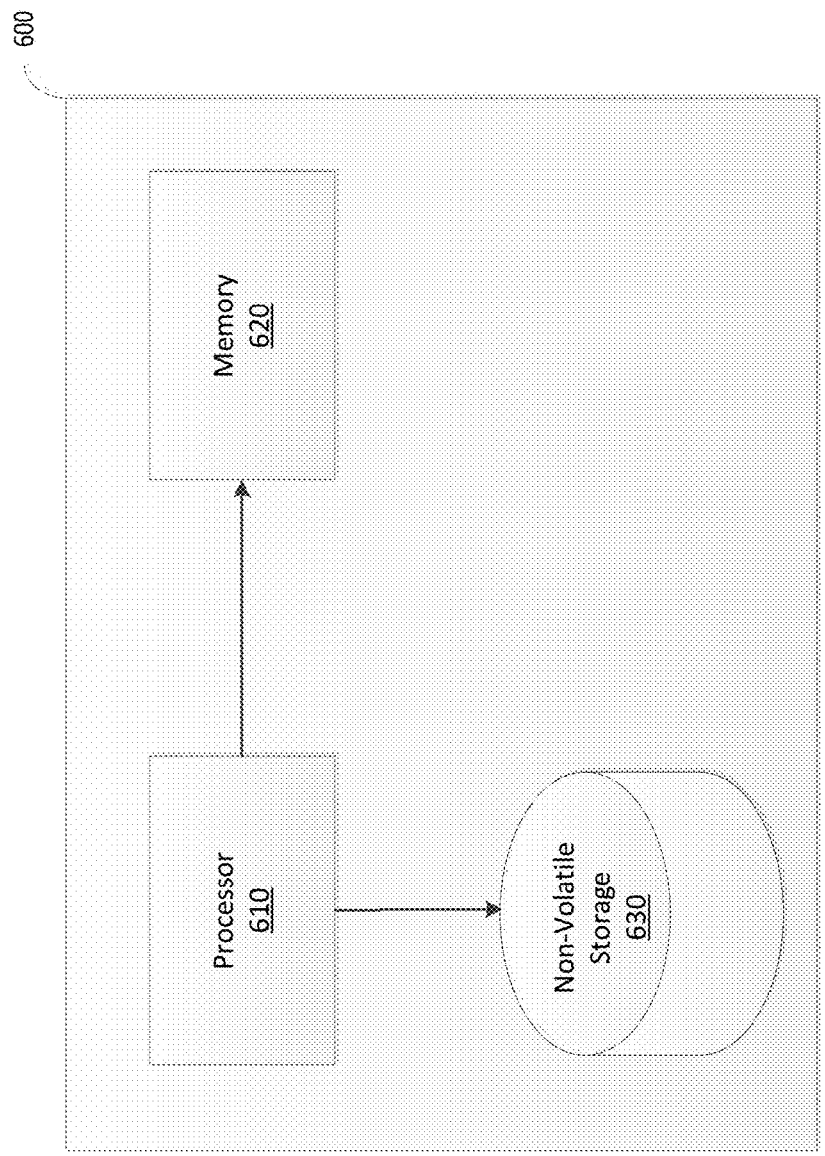
FIG. 6 is a block diagram of an illustrative computer system that may be used in implementing some embodiments of the technology described herein.

An illustrative implementation of a computer system 600 that may be used in connection with any of the embodiments of the disclosure provided herein is shown in FIG. 6. The computer system 600 may include one or more processors 610 and one or more articles of manufacture that comprise non-transitory computer-readable storage media (e.g., memory 620 and one or more non-volatile storage media 630). The processor 610 may control writing data to and reading data from the memory 620 and the non-volatile storage device 630 in any suitable manner, as the aspects of the disclosure provided herein are not limited in this respect. To perform any of the functionality described herein, the processor 610 may execute one or more processor-executable instructions stored in one or more non-transitory computer-readable storage media (e.g., the memory 620), which may serve as non-transitory computer-readable storage media storing processor-executable instructions for execution by the processor 610.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system for identifying variations in sequence data relative to reference sequence data specifying a reference genome, the system comprising:
   at least one computer hardware processor; and
   at least one non-transitory computer-readable storage medium storing processor-executable instructions that, when executed by the at least one computer hardware processor, cause the at least one computer hardware processor to perform:

aligning the sequence data to the reference sequence data specifying the reference genome to obtain aligned sequence data;

determining information specifying multiple sets of variants in the sequence data relative to the reference sequence data specifying the reference genome at least in part by:

applying a first variant identification technique to the aligned sequence data to obtain a first set of variants of the multiple sets of variants; and applying a second variant identification technique to the aligned sequence data to obtain a second set of variants of the multiple sets of variants, wherein the first variant identification technique is different from the second variant identification technique;

determining, using the information specifying the multiple sets of variants in the sequence data, a reconciled set of variants in the sequence data relative to the reference sequence data specifying the reference genome, the determining comprising:

accessing a statistical model of variant dynamics across positions of the reference sequence data specifying the reference genome, wherein the statistical model encodes information indicating a probability that a first variant associated with a first set of characteristics is present at a first position in the reference sequence data specifying the reference genome based on a second variant associated with a second set of characteristics being present at a second position in the reference sequence data specifying the reference genome;

using a Viterbi algorithm or a forward-backward algorithm for hidden Markov models to determine whether a first variant of the multiple sets of variants is present at a first position in the sequence data based, at least in part, on the statistical model and one or more variants at one or more other positions in the sequence data.

2. The system of claim 1, wherein determining whether the first variant of the multiple sets of variants is present at the first position comprises determining whether there is an insertion, a deletion, a single nucleotide polymorphism, or an inversion present at the first position in the sequence data or whether there is no variation at the first position in the sequence data relative to the reference sequence data specifying the reference genome.

3. The system of claim 1, wherein the determining comprises determining information specifying a third set of variants in the sequence data generated by using a third respective variant identification technique, wherein the third variant identification technique is different from the first and second variant identification techniques.

4. The system of claim 3, wherein the determining comprises:

determining information specifying a fourth set of variants in the sequence data generated by using a fourth variant identification technique; and determining information specifying a fifth set of variants in the sequence data generated by using a fifth variant identification technique.

5. The system of claim 1, wherein determining the reconciled set of variants comprises selecting each variant in the reconciled set of variants from the multiple sets of variants.

6. The system of claim 1, wherein determining the reconciled set of variants comprises identifying no more than one variant for each position in the sequence data.

7. The system of claim 1, wherein the processor-executable instructions further cause the at least one computer hardware processor to perform:

estimating, using training sequence data, the statistical model of variant dynamics, comprising estimating the probability that the first variant associated with the first set of characteristics is present at the first position in the reference sequence data specifying the reference genome based on the second variant associated with the second set of characteristics being present at the second position in the reference sequence data specifying the reference genome.

8. The system of claim 1, wherein determining the first variant of the multiple sets of variants at the first position is performed by using a likelihood that some variant is present at the first position in the sequence data given that a variant is present at a second position in the sequence data, wherein the second position precedes the first position in the sequence data.

9. The system of claim 1, wherein determining the first variant of the multiple sets of variants at the first position is performed by using a likelihood that a variant of a first type is present at the first position in the sequence data given that a variant of a second type is present at a second position in the sequence data, wherein the second position precedes the first position in the sequence data.

10. The system of claim 1, wherein determining the first variant of the multiple sets of variants at the first position is performed based, at least in part, on a measure of a true positive rate and/or a false negative rate of the first variant identification technique for a particular type of variant.

11. The system of claim 10, wherein the processor-executable instructions further cause the at least one computer hardware processor to perform:

estimating the true positive rate and/or the false negative rate of the first variant identification technique for the particular type of variant.

12. The system of claim 1, wherein the statistical model encodes information indicating, for each position of a set of all positions in the reference sequence data specifying the reference genome, a probability of a first type of variant being present at the position based on a second type of variant being present at a different position in the set of all positions in the reference sequence data specifying the reference genome.

13. The system of claim 12, further comprising estimating the statistical model of variant dynamics from sequence data, comprising estimating, for each position of the set of all positions in the reference sequence data specifying the reference genome, the probability of the first type of variant being present at the position based on the second type of variant being present at the different position.

14. The system of claim 1, wherein using the Viterbi algorithm or forward-backward algorithm for hidden Markov models comprises:

determining the first variant of the multiple sets of variants is present at the first position;

determining a second variant of the multiple sets of variants is present at a second position based, at least in part, on the statistical model and the first variant.

15. The system of claim 14, further comprising determining a third variant of the multiple sets of variants is present at a third position based, at least in part, on the statistical model and the second variant.

16. The system of claim 1, wherein using the Viterbi algorithm or forward-backward algorithm for hidden Markov models comprises:
- determining a first set of probabilities for the first position, comprising determining each probability of the first set based on (a) an associated possible variant in a set of possible variants and (b) the one or more variants at the one or more other positions in the sequence data;
- determining a second set of probabilities for a second position in the sequence data, comprising determining each probability of the second set based on (a) an associated possible variant in the set of possible variants and (b) the one or more variants at the one or more other positions in the sequence data; and
- determining the first variant is present at the first position and a second variant is present at the second position by maximizing a sum of log probabilities of the first set of probabilities and the second set of probabilities.

17. A method for identifying variations in sequence data relative to reference sequence data specifying a reference genome, the method comprising:
- using at least one computer hardware processor to perform:
  - aligning the sequence data to the reference sequence data specifying the reference genome to obtain aligned sequence data;
  - determining information specifying multiple sets of variants in the sequence data relative to the reference sequence data specifying the reference genome at least in part by:
    - applying a first variant identification technique to the aligned sequence data to obtain a first set of variants of the multiple sets of variants; and
    - applying a second variant identification technique to the aligned sequence data to obtain a second set of variants of the multiple sets of variants, wherein the first variant identification technique is different from the second variant identification technique;
  - determining, using the information specifying the multiple sets of variants in the sequence data, a reconciled set of variants in the sequence data relative to the reference sequence data specifying the reference genome, the determining comprising:
    - accessing a statistical model of variant dynamics across positions of the reference sequence data specifying the reference genome, wherein the statistical model encodes information indicating a probability that a first variant associated with a first set of characteristics is present at a first position in the reference sequence data specifying the reference genome based on a second variant associated with a second set of characteristics being present at a second position in the reference sequence data specifying the reference genome;
    - using a Viterbi algorithm or a forward-backward algorithm for hidden Markov models to determine whether a first variant of the multiple sets of variants is present at a first position in the sequence data based, at least in part, on the statistical model and one or more variants at one or more other positions in the sequence data.

18. The method of claim 17, wherein determining the first variant of the multiple sets of variants at the first position is performed by using a likelihood that some variant is present at the first position in the sequence data given that a variant is present at a second position in the sequence data, wherein the second position precedes the first position in the sequence data.

19. At least one non-transitory computer-readable storage medium storing processor-executable instructions that, when executed by at least one computer hardware processor, cause the at least one computer hardware processor to perform:
- aligning sequence data to reference sequence data specifying a reference genome to obtain aligned sequence data;
- determining information specifying multiple sets of variants in sequence data relative to the reference sequence data specifying the reference genome at least in part by:
  - applying a first variant identification technique to the aligned sequence data to obtain a first set of variants of the multiple sets of variants; and
  - applying a second variant identification technique to the aligned sequence data to obtain a second set of variants of the multiple sets of variants, wherein the first variant identification technique is different from the second variant identification technique;
- determining, using the information specifying the multiple sets of variants in the sequence data, a reconciled set of variants in the sequence data relative to the reference sequence data specifying the reference genome, the determining comprising:
  - generating a data structure specifying a graph of the multiple sets of variants, the graph comprising nodes representing genetic sequences and edges connecting at least some of the nodes;
  - analyzing the data structure to identify a plurality of linear sequences in the graph, wherein each linear sequence of the plurality of linear sequences corresponds to a respective path through the graph;
  - calculating, for the plurality of linear sequences, a respective plurality of measures of divergence, the calculating comprising:
    - for each linear sequence in the plurality of linear sequences, comparing the linear sequence to the reference sequence data specifying the reference genome to determine a respective measure of divergence of the linear sequence from the reference sequence data specifying the reference genome;
  - selecting a particular linear sequence from the plurality of linear sequences based on the respective plurality of measures of divergence; and
  - determining the reconciled set of variants based on the particular linear sequence.

20. The at least one non-transitory computer-readable storage medium of claim 19, wherein selecting the particular linear sequence from the plurality of linear sequences based on the respective plurality of measures of divergence comprises using a constrained Smith-Waterman alignment technique to select the particular linear sequence from the plurality of linear sequences based on the respective plurality of measures of divergence.

* * * * *

UNITED STATES PATENT AND TRADEMARK OFFICE
CERTIFICATE OF CORRECTION

PATENT NO.          : 10,600,499 B2
APPLICATION NO.     : 15/208656
DATED               : March 24, 2020
INVENTOR(S)         : Amit Jain It is certified that error appears in the above-identified patent and that said Letters Patent is hereby corrected as shown below:

In the Claims

Column 23, Claim 3, Line 50, delete "respective".

Signed and Sealed this
Ninth Day of June, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 1
catagggtgt a                                                          11
```